United States Patent
Sun et al.

(10) Patent No.: US 11,410,745 B2
(45) Date of Patent: Aug. 9, 2022

(54) DETERMINING POTENTIAL CANCER THERAPEUTIC TARGETS BY JOINT MODELING OF SURVIVAL EVENTS

(71) Applicant: International Business Machines Corporation, Armonk, NY (US)

(72) Inventors: Zhaonan Sun, Elmsford, NY (US); Zach Shahn, Brooklyn, NY (US); Ping Zhang, White Plains, NY (US); Fei Wang, Ossining, NY (US); Jianying Hu, Bronx, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 1074 days.

(21) Appl. No.: 16/011,231

(22) Filed: Jun. 18, 2018

(65) Prior Publication Data

US 2019/0384889 A1 Dec. 19, 2019

(51) Int. Cl.
*G16B 5/00* (2019.01)
*G16H 10/60* (2018.01)
(Continued)

(52) U.S. Cl.
CPC .............. *G16B 5/00* (2019.02); *G16B 20/00* (2019.02); *G16H 10/60* (2018.01); *G16H 50/30* (2018.01)

(58) Field of Classification Search
CPC .......... G16B 5/00; G16B 20/00; G16H 10/60; G16H 30/50
(Continued)

(56) References Cited

U.S. PATENT DOCUMENTS

2006/0200319 A1* 9/2006 Brown .................. G16B 20/20
702/20
2013/0296193 A1* 11/2013 Choi ..................... G16B 25/10
702/19
(Continued)

FOREIGN PATENT DOCUMENTS

CN 105701365 A 6/2016
CN 107358062 A 11/2017

OTHER PUBLICATIONS

Mordelet, Fantine et al., Prioritization of Disease Genes with Multitask Machine Learning from Positive and Unlabeled Examples. BMC Bioinformatics (Dec. 31, 2011). (Year: 2011).*
(Continued)

*Primary Examiner* — Robert R Niquette
(74) *Attorney, Agent, or Firm* — Amin, Turocy & Watson, LLP

(57) ABSTRACT

Techniques are described that facilitate determining potential cancer gene therapy targets by joint modeling of cancer survival events. In one embodiment, a computer-implemented comprises employing, by a device operatively coupled to a processor, a multi-task learning model to determine active genetic factors respectively associated with different types of cancer based on cancer survival data and patient genomic data for groups of patients that respectively survived the different types of cancer. The computer-implemented method further comprises, determining, by the device, common active genetic factors of the active genetic factors that are shared between two or more types of cancer of the different types of cancer.

20 Claims, 11 Drawing Sheets

(51) Int. Cl.
  *G16H 50/30* (2018.01)
  *G16B 10/00* (2019.01)
  *G16B 20/00* (2019.01)
(58) Field of Classification Search
  USPC .......................................................... 703/11
  See application file for complete search history.

(56) References Cited

U.S. PATENT DOCUMENTS

2017/0140123 A1* 5/2017 Ragusa .................. G16H 50/30
2019/0057182 A1* 2/2019 Klement ................ G16H 50/20

OTHER PUBLICATIONS

Li, Yongsheng et al., Comprehensive Analysis of the Functional MicroRNA-mRNA Regulatory Network Identifies miRNA Signatures Associated with Glioma Malignant Progression. BMC Bioinformatics (Apr. 11, 2013). (Year: 2013).*
International Search Report and Written Opinion received for PCT Application Serial No. PCT/IB2019/053920 dated Aug. 27, 2019, 10 pages.
Li et al., "Comprehensive analysis of the functional microRNA-mRNA regulatory network identifies miRNA signatures associated with glioma malignant progression", Nucleic Acids Research, vol. 41, No. 22, Nov. 4, 2013, pp. 1-17.
Mordelet et al., "ProDiGe: Prioritization of Disease Genes with multitask machine learning from positive and unlabeled examples", BMC Bioinformatics, vol. 12, No. 389, 2011, pp. 1-15.
Gayvert, et al., "A Computational Drug Repositioning Approach for Targeting Oncogenic Transcription Factors," Cell Rep. Jun. 14, 2016; 15(11): doi:10.1016/j.celrep.2016.05.037, 18 pages.
Chen, et al., "A miRNA-Driven Inference Model to Construct Potential Drug-Disease Associations for Drug Repositioning," vol. 2015, Article ID 406463,10 pages, http://dx.doi.org/10.1155/2015/406463.
Li, et al., "A Multi-Task Learning Formulation for Survival Analysis," 2016 ACM, ISBN 978-1-4503-4232, DOI: http://dx.doi.org/10.1145/2939672.2939857, Feb. 16, 2008, 10 pages.
Song, et al., "A Semiparametric Likelihood Approach to Joint Modeling of Longitudinal and Time-to-Event Data," Biometrics 58, pp. 742-753, Dec. 2002.
Barlow, et al., "Analysis of Case-Cohort Designs," J Clin Epidemiol vol. 52, No. 12, pp. 1165-1172, 1999.
Clark, et al., "Bioinformatics Analysis Reveals Transcriptome and microRNA Signatures and Drug Repositioning Targets for IBD and Other Autoimmune Diseases," DOI 10.1002/ibd.22958, Received for publication Feb. 9, 2012, 19 pages.
Cross, et al., "Gene Therapy for Cancer Treatment: Past, Present and Future," Clinical Medicine & Research vol. 4, No. 3: 218-227, 2006.
Shi, et al., "Integration of Multiple Genomic and Phenotype Data to Infer Novel miRNADisease Associations," PLOS One | DOI:10.1371/journal.pone.0148521 Feb. 5, 2016, 15 pages.
Cui, et al., "MicroRNA-224 promotes tumor progression in nonsmall cell lung cancer," www.pnas.org/cgi/doi/10.1073/pnas.1502068112, Feb. 2, 2015, 10 pages.
Tagscherer, et al., "MicroRNA-210 induces apoptosis in colorectal cancer via induction of reactive oxygen," DOI 10.1186/s12935-016-0321-6, 2016, 12 pages.
Tsuchiya, et al., "MicroRNA-210 Regulates Cancer Cell Proliferation through Targeting Fibroblast Growth Factor Receptor-like 1 (FGFRL1)," J. Biol. Chem. 2011, 286:10 pages.
Fang, et al., "miR-224-3p inhibits autophagy in cervical cancer cells by targeting FIP200," Scientific Reports | 6:33229 | DOI: 10.1038/srep33229, received: May 20, 2016, 11 pages.
Mircancer, "Browse miRCancer Database," Last Accessed: Mar. 14, 2018, 3 pages.
Mullenders, et al., "Loss-of-function genetic screens as a tool to improve the diagnosis and treatment of cancer," Oncogene (2009) 28, 4409-4420.
Peppercorn, et al., "Ethics of Mandatory Research Biopsy for Correlative End Points Within Clinical Trials in Oncology," vol. 28 No. 15 May 20, 2010, 6 pages.
Weinstein, et al., "The Cancer Genome Atlas Pan-Cancer analysis project," nature genetics | vol. 45 | No. 10 | Oct. 2013, 8 pages.
Lamb, et al., "The Connectivity Map: Using Gene-Expression Signatures to Connect Small Molecules, Genes, and Disease," Science 313, 1929 (2006), 8 pages.
Dang, et al., "The Role of Hypoxia-Induced miR-210 in Cancer Progression," Int. J. Mol. Sci. 2015, 16, pp. 6353-6372.
Boyerinas, et al., "The role of let-7 in cell differentiation and cancer," Endocrine-Related Cancer (2010) 17 F19-F36, 1351-0088/10/017-F19 q 2010 Society for Endocrinology Printed in Great Britain DOI: 10.1677/ERC-09-0184, 18 pages.
Zhang, et al., "Up-regulation of miR-224 promotes cancer cell proliferation and invasion and predicts relapse of colorectal cancer," 2013, 13:104, 10 pages.
Xu, et al., "Validating drug repurposing signals using electronic health records: a case study of metformin associated with reduced cancer mortality,", 10 pages.
Examination Report received for GB Patent Application Serial No. 2019896.6 dated Mar. 30, 2022, 5 pages.

* cited by examiner

ACTIVE FACTOR ASSOCIATION BY CANCER TYPE

| | Kidney | Colon | GBM | Lung |
|---|---|---|---|---|
| hsa.let.7a | | | | |
| hsa.let.7a.1 | v | v | | v |
| hsa.let.7a.2 | v | v | | v |
| hsa.let.7a.3 | v | v | | v |
| hsa.let.7b | v | v | v | v |
| hsa.let.7c | v | | v | v |
| hsa.let.7d | v | v | v | v |
| hsa.let.7e | v | v | v | v |
| hsa.let.7f | | | v | |
| hsa.let.7f.1 | v | v | v | v |
| hsa.let.7f.2 | v | | | v |
| hsa.let.7g | v | v | v | v |
| hsa.let.7i | v | v | v | v |

ACTIVE GENETIC FACTORS BY CANCER TYPE

| Cancer Type | Active Genetic Factor | Contribution Score |
|---|---|---|
| C-A | G-1 | 0.25 |
| C-A | G-2 | 0.23 |
| C-B | G-1 | 0.22 |

CANCER TYPE ASSOCIATIONS

| Cancer Type 1 | Cancer Type 2 | Association Score |
|---|---|---|
| C-A | C-B | 0.25 |
| C-A | C-C | 0.23 |
| C-B | C-D | 0.22 |

FIG. 4

DETERMINING POTENTIAL CANCER THERAPEUTIC TARGETS BY JOINT MODELING OF SURVIVAL EVENTS

BACKGROUND

This application relates to techniques for systematically determining potential cancer therapeutic targets by joint modeling of real-world patient survival events.

SUMMARY

The following presents a summary to provide a basic understanding of one or more embodiments of the invention. This summary is not intended to identify key or critical elements, or delineate any scope of the different embodiments or any scope of the claims. Its sole purpose is to present concepts in a simplified form as a prelude to the more detailed description that is presented later. In one or more embodiments described herein, systems, computer-implemented methods, apparatus and/or computer program products are presented that provide techniques for systematically determining potential cancer therapeutic targets by joint modeling of real-world patient survival events.

According to an embodiment of the present invention, a system can comprise a memory that stores computer executable components and a processor that executes the computer executable components stored in the memory. The computer executable components can comprise an active genetic factor identification component that evaluates, using a multi-task learning model, cancer survival data and patient genomic data for groups of patients that respectively survived different types of cancer to identify active genetic factors respectively associated with the different types of cancer. The computer executable components can further comprise a disease association component that determines common active genetic factors of the active genetic factors that are shared between two or more types of cancer of the different types of cancer. In some implementations, the system can further comprise a scoring component that determines, as a function of the multi-task learning model, scores for the active genetic factors that respectively represent degrees of association between the active genetic factors and the different types of cancer with which the active genetic factors are respectively associated. The system can also comprise a selection component that selects one or more active genetic factors of the active genetic factors as gene therapy targets based on the scores respectively associated with the one or more active genetic factors.

In some embodiments, the multi-task learning model models multiple tasks of determining the active genetic factors respectively associated with the different types of cancer as an optimization problem. With these embodiments, the disease association component can determine relationship parameters representative of relationships between subsets of the different types of cancer based on a number of the common active genetic factors shared between respective types of cancer included in the subsets. In some implementations, the relationship parameters can include association scores determined for the subsets based on the number of the common active genetic factors shared between the respective types of cancer included in the subsets, wherein the association scores reflect degrees to which the respective types of cancer are related. The system can further include an optimization component that updates the multi-task learning model based on the relationship parameters, thereby generating an updated multi-task learning model, and directs the active genetic factor identification component to employ the updated multi-task learning model to identify updated active genetic factors respectively associated with the different types of cancer based on the cancer survival data and the patient genomic data. In some embodiments, the disease association component can evaluate historical disease association information for the different types of cancer representative of historical relationships between subsets of the different types of cancer. With these embodiments, the optimization component can use both the historical disease association parameters and the relationship parameters to update the multi-task learning model.

In some embodiments, elements described in connection with the disclosed systems can be embodied in different forms such as a computer-implemented method, a computer program product, or another form.

DESCRIPTION OF THE DRAWINGS

FIG. 2 presents an example, non-limiting table comprising information identifying active genetic factor associations by cancer type in accordance with one or more embodiments of the disclosed subject matter.

FIG. 3 presents an example, non-limiting table comprising information identifying and scoring active genetic factors identified for different cancer types in accordance with one or more embodiments of the disclosed subject matter.

FIG. 4 presents an example, non-limiting table comprising information identifying and scoring associative relationships between different cancer types in accordance with one or more embodiments of the disclosed subject matter.

DETAILED DESCRIPTION

Figure 1:
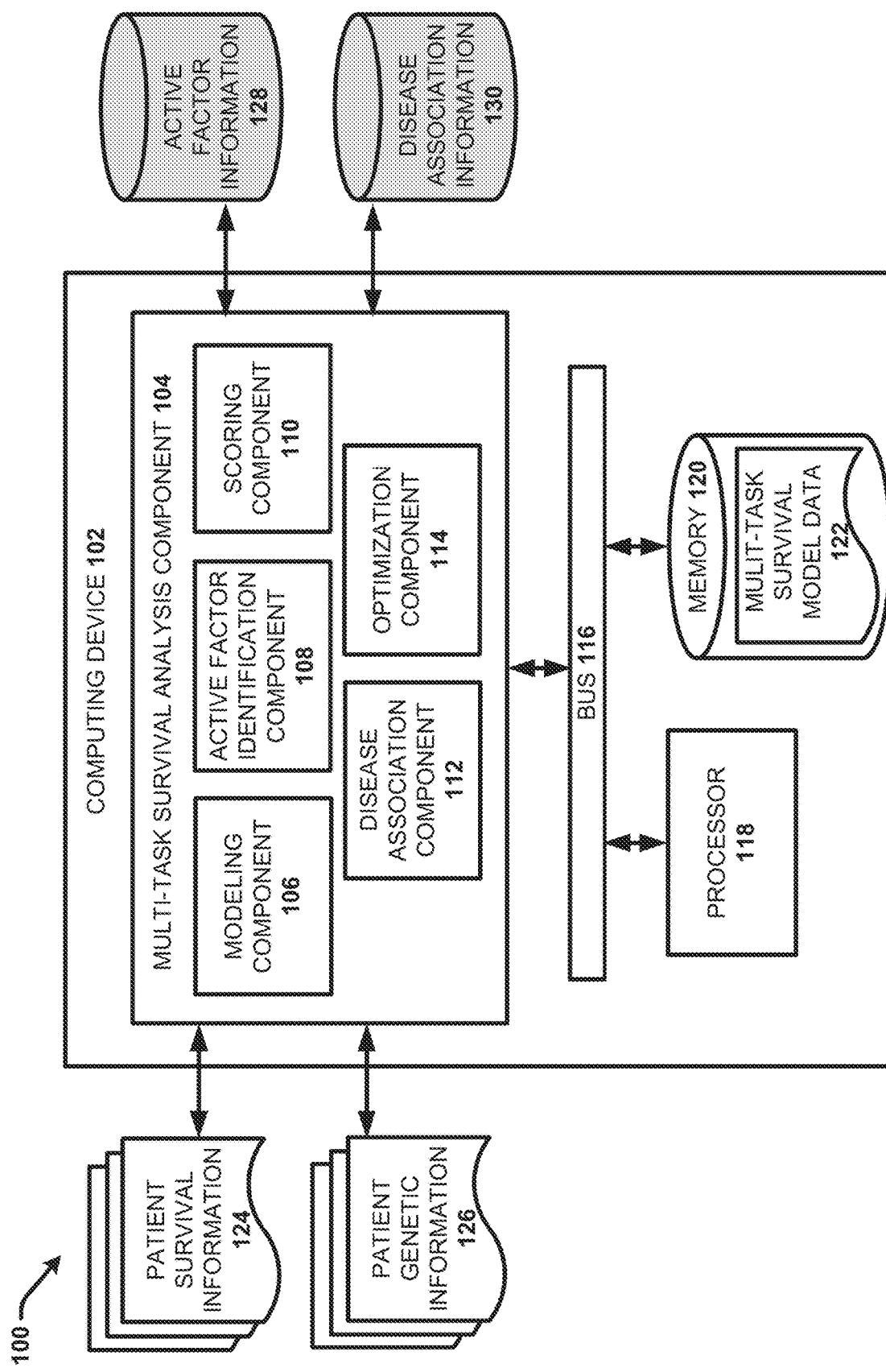
FIG. 1 illustrates a block diagram of an example, non-limiting system that facilitates systematically determining potential cancer therapeutic targets by joint modeling of real-world patient survival events in accordance with one or more embodiments of the disclosed subject matter.

The following detailed description is merely illustrative and is not intended to limit embodiments and/or application or uses of embodiments. Furthermore, there is no intention to be bound by any expressed or implied information presented in the preceding Summary section or in the Detailed Description section.

Cancer is an abnormal growth of cells, the proximate cause of which is an imbalance in cell proliferation and demise breaking through the normal physiological checks and balances system. Cancer is caused by one or more of a variety of gene alterations. Gene therapy is a form of treatment which attempts to introduce genetic materials, (e.g. deoxyribonucleic acid (DNA), ribonucleic acid (RNA), etc.), into living cells. A number of clinical trials are investigating gene therapies for specific types of cancers and new types of gene therapy treatments are continuously under development. Although gene therapy is a promising cancer treatment technique, the current development process for cancer gene therapies is based on high cost and laborious in-vitro and in-vivo clinical experiments together with pre-clinical animal models.

The subject disclosure provides systems, computer-implemented methods, apparatus and/or computer program products for systematically determining potential cancer gene therapy targets by joint modeling of real-world patient survival events. The identified potential cancer gene therapy targets can include genetic factors demonstrating a high association with a particular type of cancer as well as those which are highly associated with multiple types of cancers. As a result, high cost clinical gene therapy development can be streamlined toward gene therapies having relatively higher efficacy potential and/or that are applicable to multiple types of cancer. In particular, many different types of cancer have common genetic mechanisms, therefore different types of cancer could be associated with each other. The disclosed techniques provide a systematic way of generating a hypothesis for gene therapy targets of different types of cancer using analysis of real-world observational health data and leveraging associations between the different types of cancer. The real-world observational health data can comprise survival data of different cohorts of patients respectively diagnosed with different types of cancer and genetic information for the respective patients. In some implementations, the real-world observational health data can further incorporate existing or historical knowledge of associations between two or more types of cancer (e.g., provided in clinical literature developed through clinical trials and the like).

In one or more embodiments, the disclosed techniques employ a multi-task machine-learning survival model to formulate the task of generating hypothesis of gene therapy targets as an optimization problem. The multi-task survival model can include separate survival models for each type of cancer. Each survival model can be configured to evaluate the patient survival data and the patient genetic data for a specific type of cancer to identify genetic factors that could be attributed to the survival times of the respective patients. Genetic factors determined to have a contribution to cancer survival time (e.g., a positive contribution or a negative contribution) are referred to herein as active genetic factors. The individual survival models can be coupled to one another in a multi-task learning framework by introducing disease association parameters that define associations between two or more types of cancers. In this regard, the disclosed techniques can jointly or simultaneously solve the individual survival models for the different cancer types under a unified model framework and leverage disease-disease associations to achieve improved survival model performance. For example, in one or more embodiments, the multi-task survival model can be applied to simultaneously identify active genetic factors for each type of cancer using the separate survival models for each type of cancer. Common active genetic factors shared between two or more cancer types can then be identified and new disease association parameters can be developed based on the identified common active genetic factors. The new disease association parameters can then be used as input to optimize or update the individual survival models, thereby causing the updated survival models to provide enhanced identification of active genetic factors. This multi-task learning framework can be iteratively applied until convergence is reached. The output of the multi-task learning analysis includes information identifying active genetic factors for each type of cancer, common genetic factors shared between two or more types of cancer, as well as association parameters defining associations between two or more types of cancer.

In one or more embodiments, the process of determining the active genetic factors associated with each type of cancer can involve generating a contribution score for each associated active genetic factor. The contribution score can represent the degree to which an active genetic factor is considered to contribute to the survival time of a particular type of cancer. For example, in some implementations, a higher score for an active genetic factor in relation to a particular type of cancer can indicate a higher degree of contribution of the active genetic factor to the survival time of the type of cancer. In this regard, active genetic factors associated with a particular cancer type having relatively higher contribution scores than other active genetic factors associated with the caner type can be selected and recommended as potential gene therapy targets. Further, common active genetic factors shared between a group of two or more types of cancers and also having relatively high contribution scores can be selected as potential gene therapy targets for all types of cancers in the group. As a result, clinical development of new gene therapies can be focused on these common active genetic factors to develop new gene therapies that are applicable to multiple types of cancer (as opposed to just a single type of cancer).

One or more embodiments are now described with reference to the drawings, wherein like referenced numerals are used to refer to like elements throughout. In the following description, for purposes of explanation, numerous specific details are set forth in order to provide a more thorough understanding of the one or more embodiments. It is evident, however, in various cases, that the one or more embodiments can be practiced without these specific details.

Turning now to the drawings, FIG. 1 illustrates a block diagram of an example, non-limiting system 100 that facilitates systematically determining potential cancer therapeutic targets by joint modeling of real-world patient survival events in accordance with one or more embodiments of the disclosed subject matter. System 100 and other systems detailed herein can provide substantial technical improvements in association with identifying promising genetic targets for which to develop gene therapies against in association with treating various types of cancer.

In particular, system 100 and/or the components of system 100 (and other systems disclosed herein) can be employed to use hardware and/or software to solve problems that are highly technical in nature, that are not abstract, and that cannot be performed as a set of mental acts by a human. For example, a human could not possibly automatically (e.g., within a matter of seconds or less) and consistently evaluate a massive amount of patient survival data, genetic data, and disease association data to narrow down on promising cancer gene therapy targets. The disclose techniques provide for systematically (e.g., using machine learning) and efficiently determining promising gene therapy targets to be further investigated using in vivo and in vitro experimentation. The disclosed techniques further provide for determining gene therapy targets that are applicable to multiple types of cancers. As a result, promising and cost-effective gene therapy targets can be identified with significantly increased or enhanced processing speeds. System 100 and/or components of system 100 or other systems described herein can also be employed to solve new problems that arise through advancements in technology, computer networks, the Internet, and the like. For example, system 100 and/or components of system 100 (and other systems described herein) provide for automatically determining promising gene therapy targets in real-time based on machine learning analysis of existing patient survival data and genetic data.

Embodiments of systems described herein can include one or more machine-executable components embodied within one or more machines (e.g., embodied in one or more computer-readable storage media associated with one or more machines). Such components, when executed by the one or more machines (e.g., processors, computers, computing devices, virtual machines, etc.) can cause the one or more machines to perform the operations described. For example, in the embodiment shown, system 100 includes a computing device 102 that includes a multi-task survival analysis component 104. The multi-task survival analysis component 104 further includes a modeling component 106, an active factor identification component 108, a scoring component 110, a disease association component 112 and an optimization component 114. In this regard, the multi-task survival analysis component 104, the modeling component 106, the active factor identification component 108, the scoring component 110, the disease association component 112, and the optimization component 114 can respectively correspond to machine-executable components. System 100 also includes various electronic data sources and data structures comprising information that can be read by, used by and/or generated by the multi-task survival analysis component 104. For example, these data sources and data structures can include but are not limited to: patient survival information 124, patient genetic information 126, multi-task survival model data 122, active factor information 128 and disease association information 130.

The computing device 102 can include or be operatively coupled to at least one memory 120 and at least one processor 118. The at least one memory 120 can further store executable instructions (e.g., the multi-task survival analysis component 104, the modeling component 106, the active factor identification component 108, the scoring component 110, the disease association component 112, and the optimization component 114) that when executed by the at least one processor 118, facilitate performance of operations defined by the executable instruction. In some embodiments, the memory 120 can also store the various data sources and/or structures of system 100 (e.g., the patient survival information 124, the patient genetic information 126, the multi-task survival model data 122, the active factor information 128, and the disease association information 130). In other embodiments, the various data sources and structures of system 100 can be stored in other memory (e.g., at a remote device or system), that is accessible to the computing device 102 (e.g., via one or more networks). The computing device 102 can further include a device bus 116 that communicatively couples the various components and data sources of the computing device 102. Examples of said processor 118 and memory 120, as well as other suitable computer or computing-based elements, can be found with reference to FIG. 12, and can be used in connection with implementing one or more of the systems or components shown and described in connection with FIG. 1 or other figures disclosed herein.

In some implementations, the computing device 102, and/or the various components and data sources of system 100 can be communicatively connected via one or more networks. Such networks can include wired and wireless networks, including but not limited to, a cellular network, a wide area network (WAD, e.g., the Internet) or a local area network (LAN). For example, the computing device 102 can communicate with an external device providing the patient survival information 124 and/or the patient genetic information 126, and/or another external device to which the active factor information 128 and/or disease association information 130 is provided, (and vice versa), using virtually any desired wired or wireless technology, including but not limited to: wireless fidelity (Wi-Fi), global system for mobile communications (GSM), universal mobile telecommunications system (UMTS), worldwide interoperability for microwave access (WiMAX), enhanced general packet radio service (enhanced GPRS), third generation partnership project (3GPP) long term evolution (LTE), third generation partnership project 2 (3GPP2) ultra mobile broadband (UMB), high speed packet access (HSPA), Zigbee and other 802.XX wireless technologies and/or legacy telecommunication technologies, BLUETOOTH®, Session Initiation Protocol (SIP), ZIGBEE®, RF4CE protocol, WirelessHART protocol, 6LoWPAN (IPv6 over Low power Wireless Area Networks), Z-Wave, an ANT, an ultra-wideband (UWB) standard protocol, and/or other proprietary and non-proprietary communication protocols. The computing device 102 can thus include hardware (e.g., a central processing unit (CPU), a transceiver, a decoder), software (e.g., a set of threads, a set of processes, software in execution) or a combination of hardware and software that facilitates communicating information between the computing device 102 and externals systems, sources and devices.

In various embodiments, the multi-task survival analysis component 104 can perform machine-learning analysis of the patient survival information 124 and the patient genetic information 126 using a multi-task learning model or framework to systematically determine information regarding potential gene therapy targets that are strong candidates for developing new gene therapies for in association with treating various types of cancer. In this regard, the patient survival information 124 can include collated survival information for many (e.g., thousands, tens of thousands, hundreds of thousands, etc.) different patients diagnosed with different types of cancer. The patient survival information 124 can identify for each patient, at least the type of cancer the patient was diagnosed with and the duration of time from diagnosis to one of two events; demise or a determination that the patient has become disease free (or otherwise cleared of the cancer with which the patient was diagnosed). The cancer types represented in the patient survival information 124 can vary and can include essentially any known type of cancer. There are over one hundred known types of cancers that affect humans. Some common types of cancers that can be evaluated by system 100 can include for example: glioblastoma multiformae (GBM), lymphoblastic acute myeloid leukemia (LAML), head and neck squamous carcinoma (HNSC), lung adenocarcinoma (LUAD), lung squamous carcinoma (LUSC), breast carcinoma (BRCA), kidney renal clear-cell carcinoma (KIRC), ovarian carcinoma (OV), bladder carcinoma (BLCA), colon adenocarcinoma (COAD), uterine cervical and endometrial carcinoma (UCEC), rectal adenocarcinoma (READ), and the like.

The patient genetic information 126 can comprise genetic or omics information for each of the patients represented in the patient survival information 124. The genetic or omics information can include essentially any type of biological characteristic that could be involved in the genetic mechanism employed by one or more types of cancer. For example, the patient genetic information 126 can include but is not limited to, for each of the patients (or in some implementations one or more of the patients): DNA sequence data, gene expression data, microRNA (miRNA) expression data, copy number variation data, gene mutation data, DNA methylation data, reverse phase protein array (RPPA) data, and the like. In some implementations, the patient genetic information 126 and/or the patient survival information 124 can also include additional information about the respective patients, such as demographic information, medical history information, and the like.

In one or more embodiments, the multi-task survival analysis component 104 can determine gene therapy targets for different types of cancers by evaluating the patient survival information 124 in view of the patient genetic information 126 as a multi-task survival optimization problem. In this regard, the multi-task survival optimization problem can be modeled using a multi-task survival model. The multi-task survival model can comprise separate survival models for the different types of cancers represented in the patient survival information 124. Each of the different survival models can be configured to employ one or more machine learning analysis functions (e.g., unsupervised, supervised, neural networks, etc.) to determine correlations between genetic factors and the survival times of patients diagnosed with the respective types of cancers they are configured to evaluate. Genetic factors determined to have strong correlations to cancer survival times (e.g., relatively short survival times and/or relatively long survival times) can be recommended as potential gene therapy targets.

The multi-task survival model can further couple the different survival models together in a multi-task learning framework by introducing disease association parameters. In this regard, the multi-task survival analysis component 104 can be configured to solve the multi-task optimization problem by jointly solving the different survival models for the different cancer types under a unified model framework while exploiting commonalties and/or differences across the different survival models, thereby facilitating improved learning efficiency and prediction accuracy for the task-specific survival models when compared to training the models separately. The commonalties and differences across the different survival models can be based on learned disease association parameters, (and in some implementations known disease association parameters), that define associations and/or disassociations between two or more different types of cancer. For example, the disease association parameters can include information identifying two or more cancer types that are related, how the two or more cancer types are related (e.g., what active genetic factors they share), and/or a degree to which the two or more cancer types are related. For example, in one or more embodiments, a high-level process for solving the multi-task optimization problem can comprise identifying the active genetic factors respectively associated with the different types of cancers using the separate survival models for different types of cancers. Common active genetic factors shared between two or more types of the cancers can then be identified and disease association parameters can be determined based on the common active genetic factors. This process can further be iteratively performed using the disease association parameters determined in each iteration to optimize the performance of the separate survival models until convergence is reached.

In the embodiment shown, to facilitate performance of the multi-task survival analysis, the multi-task survival analysis component 104 can include modeling component 106, active factor identification component 108, scoring component 110, disease association component 112, and optimization component. In one or more embodiments, the modeling component 106 can facilitate applying the patient survival information 124 and the patient genetic information 126 to the multi-task survival model. For example, in some implementations, the modeling component 106 can access subsets of the patient survival information 124 and the patient genetic information 126 for different patient cohorts associated with different types of cancer. Each subset of the patient survival information 124 and the patient genetic information 126 can comprise information for patients diagnosed with a different type of cancer. The modeling component 106 can further apply the subsets of the patient survival information 124 and the patient genetic information 126 to corresponding individual survival models developed for the different cancer types. Information defining the multi-task survival model and the associated individual survival models for different the different types of cancer can be stored in memory (e.g., as multi-task survival model data 122).

In association with analysis of the patient survival information 124 and the patient genetic information 126 using the survival models, the active factor identification component 108 can identify, for each type of cancer, active genetic factors included in the patient genetic information 126 that are involved in the genetic mechanisms employed by the respective cancer types to proliferate. In this regard, the active factor identification component 108 can identify active genetic factors based on observed correlations between genetic factors and the cancer survival times provided in the patient survival information 124. For example, a genetic factor that is frequently observed in association with short survival times of a specific type of cancer and less frequently observed in association with long survival times of the specific type of cancer can be identified as an active genetic factor having an active role in the genetic mechanism of the specific type of cancer.

The active factor identification component 108 can further employ disease association parameters regarding associations between different cancer types to facilitate identifying the active genetic factors associated with the different cancer types. For example, cancer types which are highly associated can share one or more common critical underlying genetic factors. By leveraging disease association information, the survival models of associated cancer types could borrow information from each other, thereby facilitating more efficient and accurate identification of active genetic factors across the all types of cancer. In various embodiments, as discussed further below, the disease association parameters applied by the active factor identification component 108 to facilitate identifying active genetic factors are determined by the disease association component 112 under the multi-task survival analysis model. In the embodiment shown, the disease association parameters determined by the disease association component 112 can be stored in a database identified as disease association information 130. In this regard, the active factor identification component 108 can access the disease association information 130 to facilitate identifying the active genetic factors associated with different cancer types. In other embodiments, (discussed infra with reference to FIG. 6), historical or known disease association parameters can also be employed by the active factor identification component 108 to facilitate identifying active genetic factors associated with different types of cancer. The individual survival models can employ one or more machine learning algorithms to facilitate the identification of the active genetic factors respectively associated with a particular type of cancer based on the patient survival information 124, and the patient genetic information 126 and the disease association parameters.

In some embodiments, in association with identification of the active genetic factors associated with each cancer type, the scoring component 110 can determine contribution scores for the active genetic factors. The contribution score for an active genetic factor with respect to a specific type of cancer can reflect a degree to which the active genetic factor contributes to the survival time of the specific type of cancer, which in turn reflects a degree to which the active genetic factor plays a role in the genetic mechanism of the specific type of cancer. For example, the contribution scores can be based on a frequency with which a particular genetic factor is identified for patients diagnosed with a specific cancer type. In another example, the contribution score can be based on a frequency with which an active genetic factor is identified in association with a specific survival time of patients diagnosed with a specific cancer type. For example, the survival time can be less than a defined threshold, greater than a defined threshold, and the like. In some implementations, the higher the contribution score associated with a particular active genetic factor and cancer type, the greater the contribution of the active genetic factor to the cancer survival time, (and thus the greater the contribution of the active genetic factor to the genetic mechanism performed by the cancer type to proliferate).

Information regarding active genetic factors identified for respective types of cancer and contribution scores determined for the active genetic factors can be collated in a suitable data structure. For example, in the embodiment shown, information determined by the active factor identification component 108 and/or the scoring component 110 regarding identified active genetic factors for different types of cancers can be organized in a database identified as active factor information 128.

FIG. 2 presents an example, non-limiting table 200 comprising information identifying active genetic factor associations by cancer type in accordance with one or more embodiments of the disclosed subject matter. In particular, table 200 identifies 13 types of miRNA genetic factors included in the let-7 family (e.g., has.let.7a, hsa.let.7a.1, has.let.7a.2, etc.). The let-7 miRNA family has been found to be related to cell differentiation. Table 200 further identifies four different types of cancer, including kidney, colon, CBM and lung cancer. A check mark is provided for respective cancer types and miRNA genetic factor combinations to identify that the cancer type is associated with the miRNA genetic factor. As shown in table 200, many of the different miRNA genetic factors of the let-7 family are associated with two or more types of cancers. For example, in the embodiment shown, has.let.7a.1 is associated with kidney, colon and lung cancer. Table 200 provides one example of the type of active genetic factor information that can be determined by the active factor identification component 108 in accordance with one or more embodiments. In this regard, table 200 and/or information similar to that provided by table 200 can be provided by the active factor information 128.

FIG. 3 presents an example table 300 comprising information that can be determined by the active factor identification component 108 and the scoring component 110 in accordance with one or more embodiments described herein. In this regard, table 300 and/or information similar to that provided by table 300 can also be provided in the active factor information 128. Table 300 comprises information identifying and scoring active genetic factors identified for different cancer types in accordance with one or more embodiments of the disclosed subject matter. In the embodiment shown, each row of table 300 corresponds to a specific cancer type and active genetic factor combination. For example, the first row corresponds to cancer type A (C-A) and active genetic factor 1 (G-1). The second row corresponds to cancer type A (C-A) and active genetic factor 2 (G-1). The third row corresponds to cancer type B (C-B) and active genetic factor 1 (G-1). Table 300 further include a score column that provides a contribution score (e.g., as determined by scoring component 110) for each cancer type and active genetic factor combination. The contribution score reflects a degree to which the active genetic factor is considered to contribute to the genetic mechanism of the corresponding cancer type to proliferate. In this regard, a higher contribution score value indicates a higher potential for the active genetic factor to be a strong gene therapy target for the corresponding cancer type.

With reference again to FIG. 1, in various embodiments, the disease association component 112 can evaluate the active genetic factors identified for each of the different types of cancer by the active factor identification component 108 to determine common active genetic factors shared between two or more cancer types. The disease association component 112 can further generate disease association information 130 regarding relationships between two or more types of cancer based at least in part on the common active genetic factors shared between them. For example, with reference again to table 200, the disease association component 112 can determine that kidney cancer, colon cancer, and lung cancer are related because they share active genetic factor has.let.7a.1. In various embodiments, the disease association component 112 and/or the scoring component 110 can further determine a degree to which two or more cancer types are related. The disease association component 112 and/or the scoring component 110 can further generate an association score for the group of the two or more cancer types that reflects the degree to which the two or more cancer types are associated. For example, a higher association score can indicate a stronger association between the two or more type of cancer relative to a lower association score.

For example, FIG. 4 presents an example table 400 comprising information that can be determined by the disease association component 112 and/or the scoring component 110 in accordance with one or more embodiments described herein. In this regard, table 400 and/or information similar to that provided by table 400 can be provided by the disease association information 130. Table 400 comprises information identifying and scoring associative relationships between different cancer types in accordance with one or more embodiments of the disclosed subject matter. For example, the cancer pair C-A and C-B have an association score of 0.25, the cancer pair C-A and C-C have an association score of 0.23, and the cancer pair C-B and C-D have an association score of 0.22.

With reference back to FIG. 1, in various embodiments, the disease association component 112 and/or the scoring component 110 can determine an association score representative of a degree to which two or more cancer types are related based on the number of common active genetic factors shared between the two or more cancer types. In this regard, the greater the number of common active genetic factors, the greater the association between the respective cancers, and the higher the association score. For example, with reference again to table 200, with respect to the let-7 family, kidney cancer and lung cancer share a greater number of common active genetic factors relative to kidney cancer and colon cancer. According to this example the association score for the combination of kidney and lung cancer can be higher than the association score for the combination of kidney and colon cancer.

In some implementations, the disease association component 112 and/or the scoring component 110 can further determine the association score for two or more type of cancer based on the contribution scores respectively associated with the genetic factors shared between the cancer types. In this regard, genetic factors with higher contribution scores can be given greater weight than those with lower contribution scores. For example, assume cancer type D (C-D) and cancer type E (C-E), share active genetic factors G-1 and G-2. According to this example, the association score can be based on the combined contribution scores associated with each cancer type and genetic factor pair, wherein the higher the collective contribution score, the higher the association score. For instance, assume C-D and G-1 have a contribution score of 0.25, C-E and G-1 have a contribution score of 0.30, C-D and G-2 have a contribution score of 0, 15, and C-E and G-2 have a contribution score of 0.75. According to this example, the combined contribution score would be 1.45 (e.g., 0.25+0.30+0.15+0.75). In another embodiment, the degree of association between two or more types of cancer can also be based on a difference or degree of deviation between the contribution scores associated with common active genetic factors. For instance, in furtherance to the above example, the contribution scores for G-1 with respect to C-D and C-E deviate only slightly, with a difference of only 0.5. However, the contributions scores for G-2 with respect to C-D and C-E greatly deviate, with a difference of 0.6. According to this example, the association score determined for the cancer type pair C-D/C-E can be adjusted or penalized based on the high degree of deviation between the contribution scores for G-2.

As noted above, in various embodiments, the multi-task survival model can be formulated and/or evaluated as an optimization problem. In this regard, in one or more embodiments, using the respective survival models for the different cancer types, the active factor identification component 108 and the scoring component 110 can initially determine active genetic factors and the active genetic factor contribution scores for different cancer types based on the patient survival information 124 and the patient genetic information 126. The disease association component 112 and/or the scoring component 110 can then determine initial disease association parameters based on common active genetic factors share between two or more types of cancer. With these embodiments, after the initial active genetic factors and initial disease association parameters are determined, the initial disease association parameters can be fed back into the multi-task survival model and used to optimize the performance and efficiency of the individual survival models. In this regard, the optimization component 114 can use the initial disease association parameters to update and/or optimize one or more of the individual survival models. The updated survival models can be stored in the multi-task survival model data 122. The active factor identification component 108, scoring component 110 and disease association component 112 can then repeat the multi-task survival analysis using the updated survival models to determine updated active genetic factors, updated active genetic factor contribution scores, and updated disease association parameters based on the patient survival information 124 and the patient genetic information. The active factor identification component 108, scoring component 110, disease association component 112 and optimization component can further iteratively repeat this survival analysis and model updating/optimizing process based on the new disease association parameters determined after each iteration until convergence is reached.

In one or more embodiments, the optimization component 114 can determine when convergence is reached based on a degree of change between a current model output and the previous model output. For example, assuming the current output of the model is represented by information data set k, the optimization component can compare the information data set k, with information data set k−1. If the difference between k and k−1 is less than or equal to a defined degree of deviation, then the optimization component can determine convergence has been reached. The final data set k, and then be stored. In this regard, the output data of each iteration will include, for each type of cancer, identified active genetic factors associated with the cancer type and the contribution scores for the active genetic factors. The output data of each iteration will also include updated disease association parameters. Accordingly, the optimization component 114 can determine when convergence has been reached based on little or no change to currently determined active genetic factors, contribution scores for the active genetic factors, and disease association parameters, relative to active genetic factors, contribution scores for the active genetic factors, and disease association parameters determined from a previous iteration.

Figure 5:
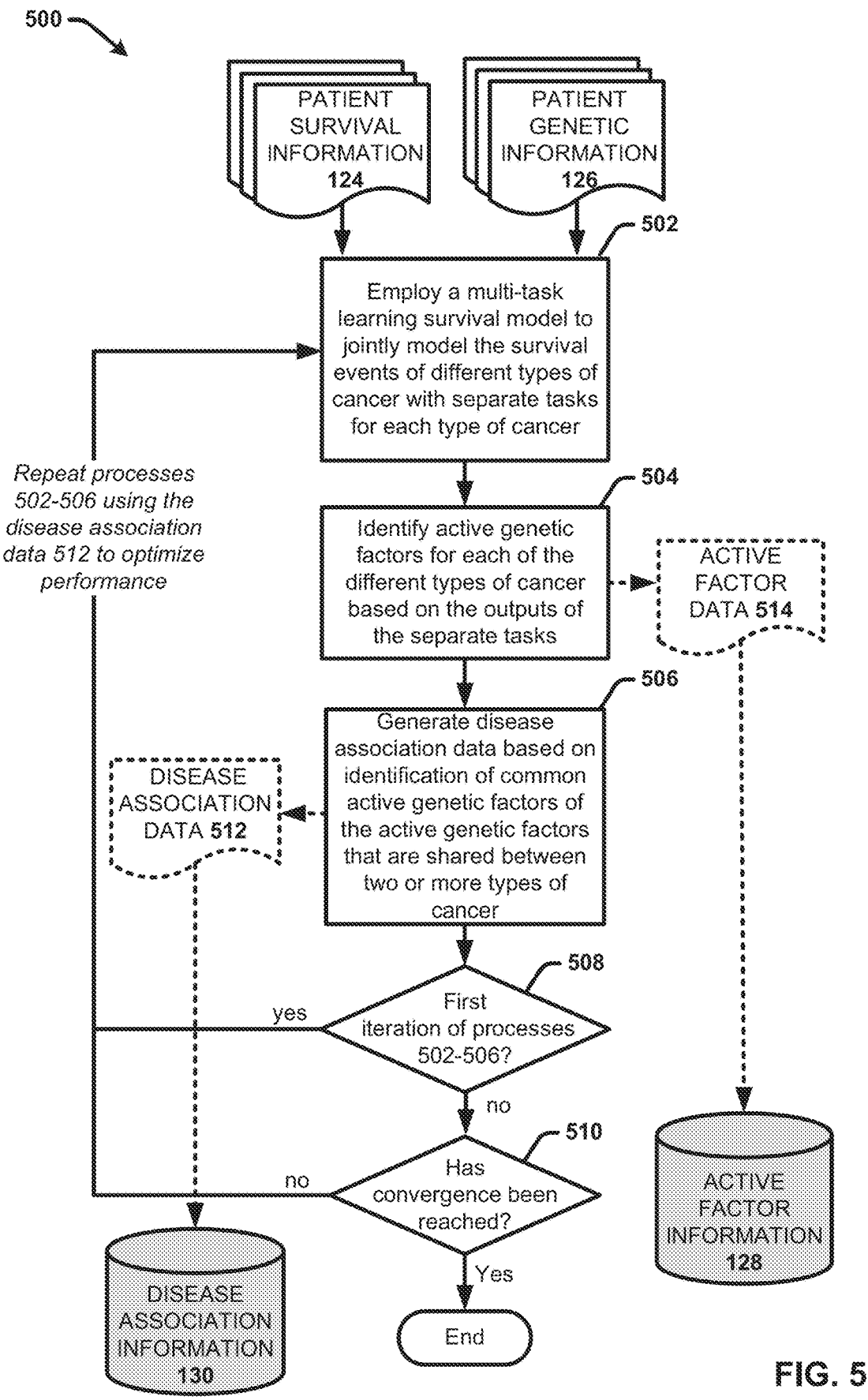
FIG. 5 provides a high-level flow diagram of an example computer-implemented process for determining potential cancer therapeutic targets by joint modeling of real-world patient survival events in accordance with one or more embodiments of the disclosed subject matter.

FIG. 5 provides a high-level flow diagram of an example computer-implemented process 500 for determining potential cancer therapeutic targets by joint modeling of real-world patient survival events in accordance with one or more embodiments of the disclosed subject matter. In this regard, process 500 reflects an example implementation of the multi-task survival analysis that can be performed by the multi-task survival analysis component 104 to determine the disease association information 130 and active factor information 128 in accordance with one or more embodiments of the disclosed subject matter. Repetitive description of like elements employed in respective embodiments is omitted for sake of brevity.

Using the patient survival information 124 and the patient genetic information 126 as input, at 502 a multi-task learning survival model can be employed to jointly model the survival events of different types of cancer with separate tasks for each type of cancer (e.g., by the modeling component 106). At 504, active genetic factors for each of the different types of cancer are identified based on the outputs of the separate tasks (e.g., by the active factor identification component 108). The identified active genetic factors can be represented by the active factor data 514. In some embodiments, the active factor data 514 can include contribution scores determined for the respective active genetic factors. In one or more embodiments, the active factor data 514 can be added to the active factor information 128 and stored. At 506, disease association data 512 can be generated based on identification of common active genetic factors of the active genetic factors that are shared between two or more types of cancer (e.g., via the disease association component 112). For example, the disease association component 112 can process the active factor data 514 to identify one or more common active genetic factors shared between a group consisting of two or more types of cancer. The disease association component 112 and/or the scoring component 110 can also determine association scores representative of degrees of association between two or more types of cancer based in part on the number of common active genetic factors shared between them. The disease association data 512 can thus comprise disease association parameters defining relationships between different subsets of the different types of cancers evaluated by process 500. The disease association data 512 can also be added to the disease association information 130 and stored.

At 508, it is determined whether the active factor data 514 and the disease association data 512 are a result of the first iteration of processes 502-506. If so, the multi-task learning analysis is continued by repeating processes 502-506 using the disease association data 512 to optimize performance. In this regard, the disease association data 512 can be used to optimize or update the survival models for the separate tasks (e.g., via the optimization component 114), and processes 502-506 can be repeated using the updated survival models and the (original) patient survival information 124 and patient genetic information 126 as input. Each time processes 502-506 are repeated, updated active factor data 514 and disease association data 512 will be generated.

At 508, if it is determined that the active factor data 514 and the disease association data 512 are not a result of the first iteration of processes 502-506, then at 510, it is determined whether convergence has been reached. For example, the optimization component 114 can compare the current disease association data 512 and the current active factor data 514 to the disease association data and active factor data determined in the previous iteration of processes 502-506. If the degree of change between the previous data set and the current data set is less than a threshold degree of deviation, than the optimization component 114 can determine that convergence has been reached, and process 500 can end. The final disease association data 512 and active factor data 514 that is then stored in the disease association information 130 and active factor information 128, respectively, will reflect the optimal solution to multi-task survival problem. If it is determined at 510 that convergence has not been reached, then process 500 can again repeat processes 502-506 using the updated disease association data until convergence is reached.

Figure 6:
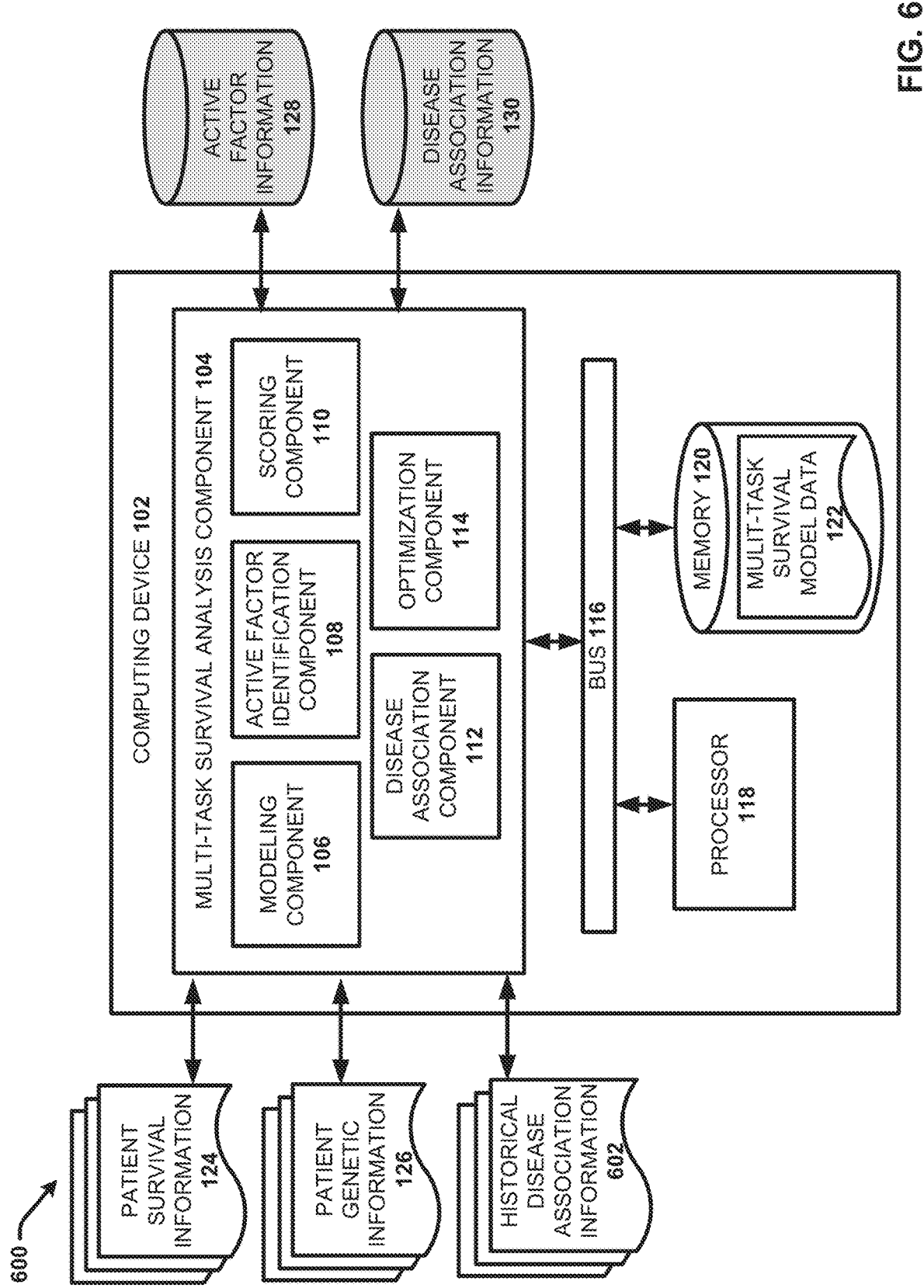
FIG. 6 illustrates a block diagram of another example, non-limiting system that facilitates systematically determining potential cancer therapeutic targets by joint modeling of real-world patient survival events in accordance with one or more embodiments of the disclosed subject matter.

FIG. 6 illustrates a block diagram of another example, non-limiting system 600 that facilitates systematically determining potential cancer therapeutic targets by joint modeling of real-world patient survival events in accordance with one or more embodiments of the disclosed subject matter. System 600 comprises same or similar features and functionalities as system 100 with the addition of historical disease association information 602. Repetitive description of like elements employed in respective embodiments is omitted for sake of brevity.

The historical disease association information 602 can include information regarding known associations between two or more types of cancer prior to the performance of the multi-task survival analysis by the multi-task survival analysis component 104. For example, in some implementations, the historical disease association information 602 can identify active genetic factors known to be associated with two or more different types of cancers, groups of two or more related types of cancers, degrees of relatedness of two or more types of cancers, and the like. The historical disease association information 602 can provided by clinical various clinical research data sources. For example, the historical disease association information 602 can be developed from existing scientific reports, white papers, open source miRNA cancer databases, and the like. In some implementations, the disease association component 112 can access various data sources comprising information regarding active genetic factors associated with specific cancer types, and employ one or more machine learning techniques to determine defined historical disease association information based on the existing clinical research.

In some embodiments, the multi-task survival analysis component 104 can use the historical disease association information 602 to further enhance or optimize the performance of the multi-task survival analysis. In this regard, the historical disease association information 602 can be used in addition to the patient survival information 124 and the patient genetic information 126 as input to the multi-task survival model. Accordingly, the historical disease association information 602 can be used to couple the individual survival models to one another at the first iteration of analysis.

Figure 7:
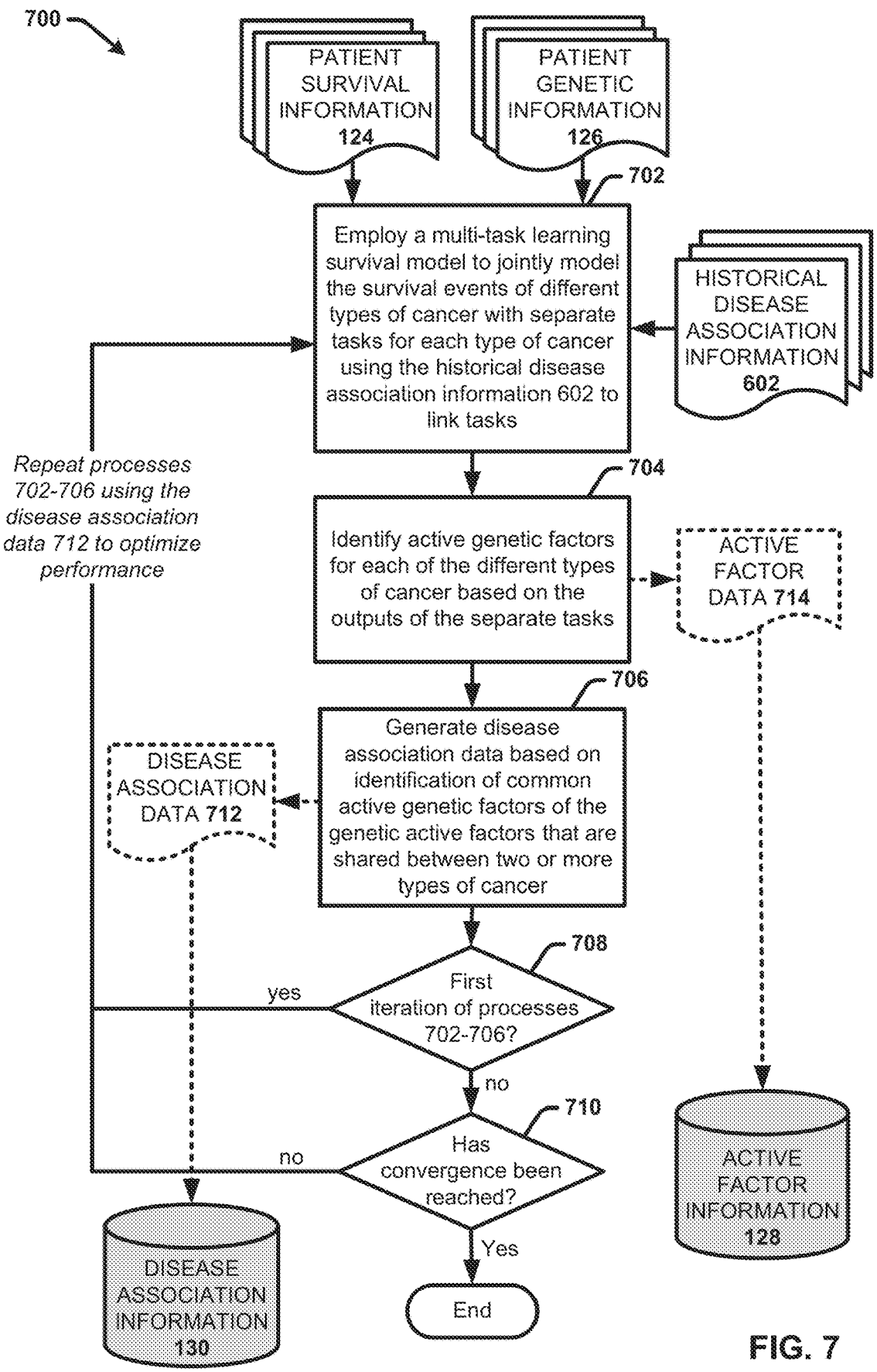
FIG. 7 provides a high-level flow diagram of another example computer-implemented process for determining potential cancer therapeutic targets by joint modeling of real-world patient survival events in accordance with one or more embodiments of the disclosed subject matter.

For example, FIG. 7 provides a high-level flow diagram of another example computer-implemented process 700 for determining potential cancer therapeutic targets by joint modeling of real-world patient survival events in accordance with one or more embodiments of the disclosed subject matter. Process 700 is substantially similar to process 500 with the addition of the historical disease association information 602 as input. Repetitive description of like elements employed in respective embodiments is omitted for sake of brevity.

At 702, the patient survival information 124, the patient genetic information 126, and the historical disease association information 602 are used as input to a multi-task learning survival model. The multi-task survival model uses the to jointly model the survival events of different types of cancer with separate tasks for each type of cancer (e.g., by the modeling component 106). The historical disease association information 602 can be used to link two or more of the respective tasks. At 704, active genetic factors for each of the different types of cancer are identified based on the outputs of the separate tasks (e.g., by the active factor identification component 108). The identified active genetic factors can be represented by the active factor data 714. In some embodiments, the active factor data 714 can include contribution scores determined for the respective active genetic factors. In one or more embodiments, the active factor data 714 can be added to the active factor information 128 and stored. At 706, disease association data 712 can be generated based on identification of common active genetic factors of the active genetic factors that are shared between two or more types of cancer (e.g., via the disease association component 112). For example, the disease association component 112 can process the active factor data 714 to identify one or more common active genetic factors shared between a group consisting of two or more types of cancer. The disease association component 112 and/or the scoring component 110 can also determine association scores representative of degrees of association between two or more types of cancer based in part on the number of common active genetic factors shared between them. The disease association data 712 can thus comprise disease association parameters defining relationships between different subsets of the different types of cancers evaluated by process 700. The disease association data 712 can also be added to the disease association information 130 and stored.

At 708, it is determined whether the active factor data 714 and the disease association data 712 are a result of the first iteration of processes 702-706. If so, the multi-task learning analysis is continued by repeating processes 702-706 using the disease association data 712 to optimize performance. In this regard, the disease association data 712 can be used to optimize or update the survival models for the separate tasks (e.g., via the optimization component 114), and processes 702-706 can be repeated using the updated survival models and the (original) patient survival information 124 and patient genetic information 126 as input. Each time processes 702-706 are repeated, updated active factor data 714 and disease association data 712 will be generated.

At 708, if it is determined that the active factor data 714 and the disease association data 712 are not a result of the first iteration of processes 702-706, then at 710, it is determined whether convergence has been reached. For example, the optimization component 114 can compare the current disease association data 712 and the current active factor data 714 to the disease association data and active factor data determined in the previous iteration of processes 702-706. If the degree of change between the previous data set and the current data set is less than a threshold degree of deviation, than the optimization component 114 can determine that convergence has been reached, and process 700 can end. The final disease association data 712 and active factor data 714 that is then stored in the disease association information 130 and active factor information 128, respectively, will reflect the optimal solution to multi-task survival problem. If it is determined at 710 that convergence has not been reached, then process 700 can again repeat processes 702-706 using the updated disease association data until convergence is reached.

Figure 8:
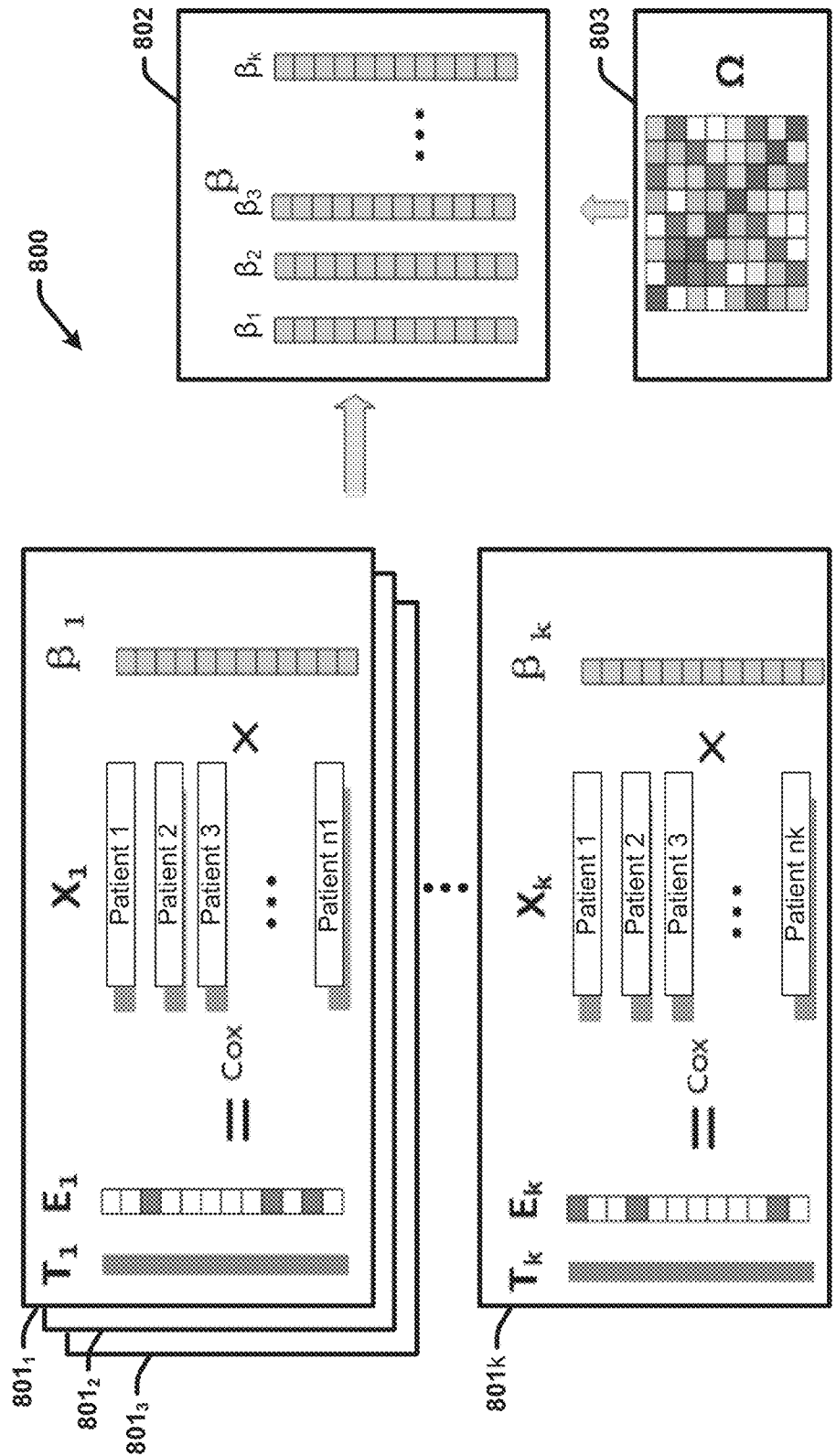
FIG. 8 illustrates an example implementation of the multi-task survival analysis framework in accordance in accordance with one or more embodiments of the disclosed subject matter.

FIG. 8 illustrates an example implementation of the multi-task survival analysis framework 800 in accordance with one or more embodiments of the disclosed subject matter. Repetitive description of like elements employed in respective embodiments is omitted for sake of brevity.

In the embodiment shown, the multi-task survival analysis framework 800 can include a plurality of survival models $801_1$-$801_k$ for a plurality of cancer types in a set of cancer types 1-k. In this regard, each type of cancer is modeled using a separate survival model. The number of cancer types k included in the set can vary. The symbol i is used in the coefficient legend to represent any single specific type of cancer in the set 1-k. The survival models for each type of cancer can be used to determine a coefficient vector $\beta_i$ as a function of the survival times for respective patients included in the cancer type group and the genetic characteristics associated with the respective patients. The $\beta_i$ coefficient vector can include a plurality of elements that respectively correspond to a genetic factor. For example, in the embodiment shown, the elements are represented by blocks and each block can correspond to a different genetic factor. Each (or in some implementations one or more) genetic factor can be associated with a contribution score that represents the contribution of the genetic factor to the survival time, wherein higher absolute scores reflect a higher contribution and lower absolute scores reflect a lower contribution. The coefficient vectors $\beta_i$ for each type of cancer can be used to determine the active genetic factors that could be potential gene therapy targets. In this regard, for each type of cancer there will be one coefficient vector $\beta_i$ that represents the contribution of different genetic elements observed in the group that are associated with the proliferation of the cancer type.

For the multi-stack survival analysis, these coefficient vectors $\beta_1$ to $\beta_k$ can be stacked together in a coefficient matrix β 802 using disease association parameters for one or more cancer types respectively represented by the individual coefficient vectors $\beta_1$-$\beta_k$. The coefficient matrix β 802 can be employed to facilitate better identification of the active genetic factors and/or the contribution scores the active genetic factors associated with each type of cancer. For example, in one or more embodiments, new hypothesis of genetic factors that could be potential gene therapy targets can be determined by thresholding on β. In the embodiment shown, the disease association parameters are represented by the disease association matrix Ω 803. In some embodiments, the disease association matrix Ω can be optionally initialized using historical or known disease association information (e.g., historical disease association information 602). In other embodiments, the disease association matrix Ω 803 can be generated based on common active genetic factors shared between two or more caner types as determined based on the active genetic factors identified for each cancer type after a first iteration of the multi-task survival analysis. The ultimate parameters of interest of the multi-stack analysis framework are an optimized coefficient matrix β 802 and disease association matrix Ω 803.

In one or more embodiments, the multi-task survival analysis framework 800 can be represented by the following partial likelihood objective function:

$$\min_{\beta,\Omega} f = \ell(T, E, X, \beta) + \frac{\lambda_1}{2} tr(\beta \Omega^{-1} \beta^\top) + \lambda_2 \|\beta\|_1.$$

$$l(t_j, e_j, X, \beta_j) = \sum_{t_i} \left( x_{(i)} \beta_j - \log \sum_{i' \in R_i} \exp(x_{(i')} \beta_j) \right)$$

The Objective Function wherein,
l(T,E,X,β) represents the partial likelihood from individual Cox models, the coefficient matrix β

$$\frac{\lambda_1}{2} tr(\beta \Omega^{-1} \beta^\top)$$

represents the prior model for β to couple tasks together, the disease association matrix Ω, and $\lambda_2 \|\beta\|_1$ represents the sparsity assumption on β, or the L1 regularizer to identify therapeutic target for each type of cancer.

In one or more embodiments, the multi-task survival analysis component 104 can be configured to solve the Objective Function above using a block coordinate descent (BCD) procedure by initializing β(0) and Ω(0). The multi-task survival analysis component 104 can further iterate or repeat solving the Objective Function until convergence is reached, each time updating β by identifying common active genetic factors by comparing sparsity patterns of columns of β, and updating Ω, the disease association information, using the patient survival information 124 and the patient genetic information 126.

Figure 9:
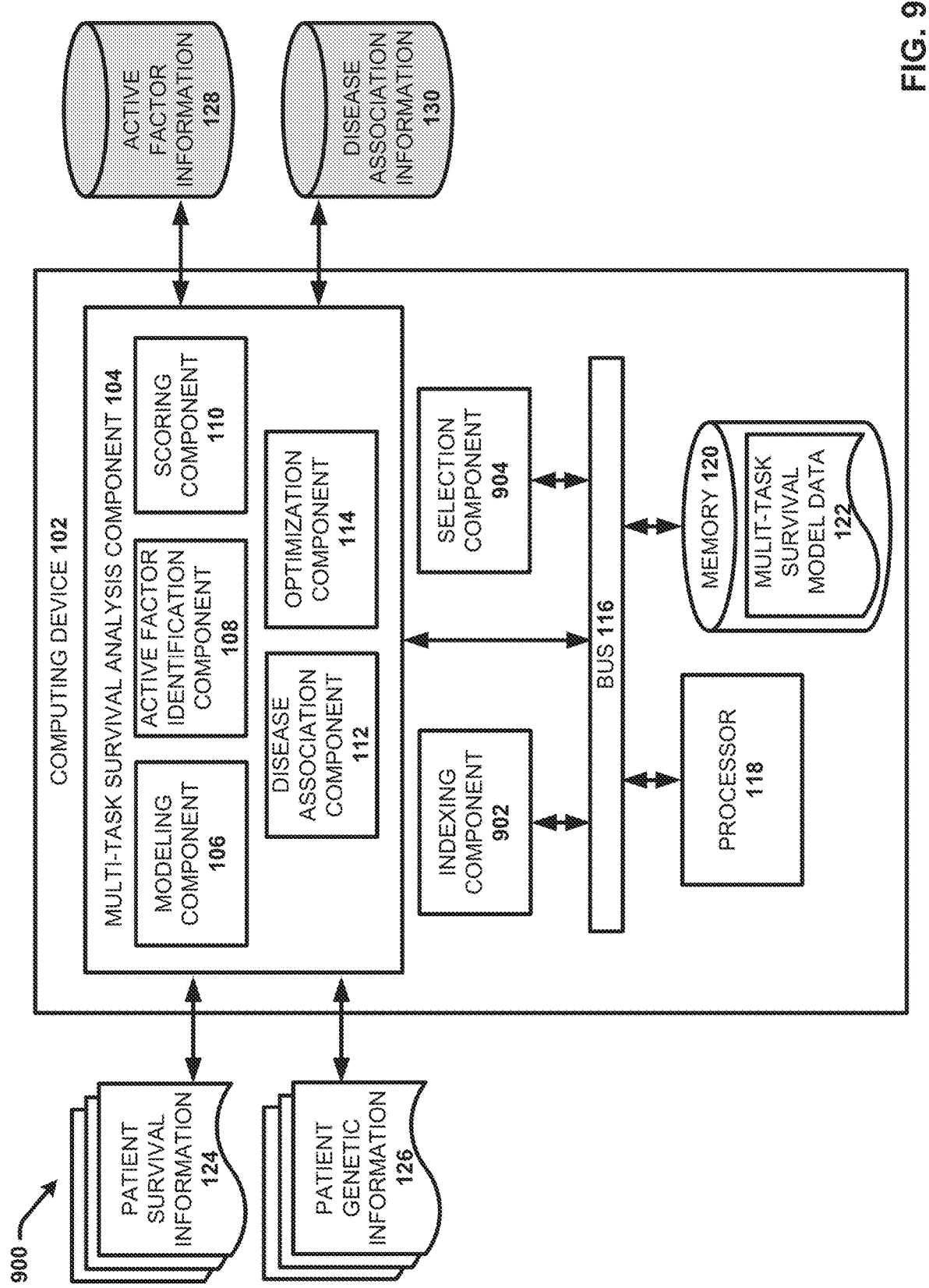
FIG. 9 illustrates a block diagram of another example, non-limiting system that facilitates systematically determining potential cancer therapeutic targets by joint modeling of real-world patient survival events in accordance with one or more embodiments of the disclosed subject matter.

FIG. 9 illustrates a block diagram of another example, non-limiting system 900 that facilitates systematically determining potential cancer therapeutic targets by joint modeling of real-world patient survival events in accordance with one or more embodiments of the disclosed subject matter. Repetitive description of like elements employed in respective embodiments is omitted for sake of brevity.

System 900 can include same or similar features as system 100 with the addition of indexing component 902 and selection component 904. In one or more embodiments, the indexing component 902 can generate one or more indexed data structures comprising the active factor information 128 and/or the disease association information 130 determined by the multi-task survival analysis component 104. For example, the indexing component 902 can generate table 200, table 300, table 400 and the like. The selection component 904 can further employ one or more of the indexed data structures to facilitate efficient selection and recommendation of one or more specific active genetic factors that are strong gene therapy targets.

In this regard, in some embodiments, the indexing component 902 can generate a first database that identifies, for each type of cancer (or in some embodiments one more types) of a plurality of different types of cancer, the active genetic factors that are were determined to be associated with the type of cancer by the active factor identification component 108. In some implementations, the first database can further include the contribution scores determined for the respective active genetic factors by the scoring component 110. For example, the first database can be provided in the active factor information 128 or another suitable data source. In one or more embodiments, using the first database, the selection component 904, can select one or more active genetic factors associated with one or more cancer types for recommending as a promising gene therapy target. For example, in one embodiment, the selection component 904 can be configured to select the active genetic factors having contributions scores above a defined threshold score. In this regard, the selection component 904 can select a subset of the active factors associated with each type of cancer having contribution scores above the defined threshold. In another implementation, the selection component 904 can be configured to select a subset of active genetic factors associated with a particular type of cancer having relatively higher contribution scores than other active genetic factors associated with the cancer type. For example, the selection component 904 can select the top N or top X percent of active genetic factors for recommending as gene therapy targets.

The indexing component 902 can also generate a second database that identifies common active genetic factors or gene therapy targets that are shared between two or more types of cancer. This second database can be provided in the disease association information 130 or another suitable data source. For example, the indexing component 902 can generate a database that identifies active genetic factors and/or gene therapy targets and then lists the types of cancers respectively associated therewith. In some embodiments, the cancer types associated with a specific active genetic factor can be ranked according to the contribution scores to indicate the degree to which each type of cancer is associated with the active genetic factor. The indexing component 902 can further rank the respective active genetic factors based on number of cancers associated therewith. In some implementations, the indexing component 902 can further rank the respective active genetic factors as a function of the number of different cancer types associated therewith and the contribution scores associated with the different cancer types and the active genetic factor. In one or more embodiments, the selection component 904 can be configured to select one or more active genetic factors for recommending as potential gene therapy targets based on the number of cancer types associated therewith and/or the contribution scores.

The indexing component 902 can also generate a third indexed data structure that identifies relationships between two or more different types of cancer. The third indexed data structure can be provided in the disease association information 130 or another suitable data source. For example, the third indexed data structure can identify cancer groups comprising two or more types of related cancers. The cancer groups can also include an association score that reflects the degree of association between the respective cancer types included in the group (e.g., as determined by the disease association component 112 and/or the scoring component 110).

Figure 10:
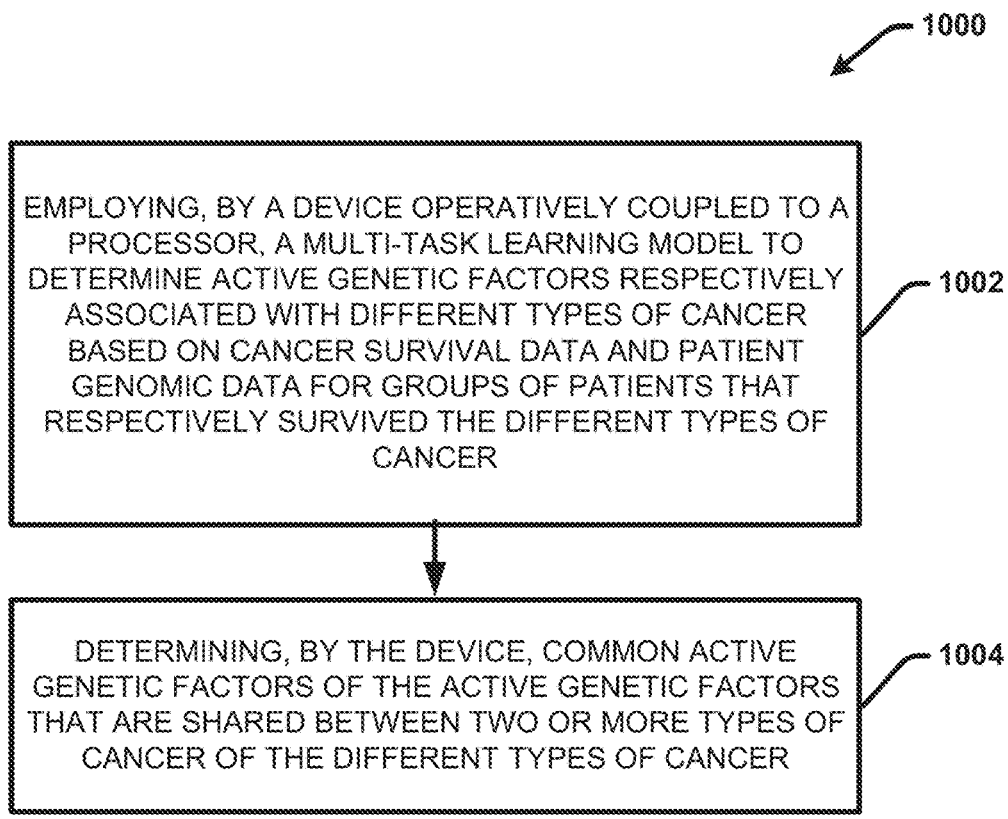
FIG. 10 provides a high-level flow diagram of another example computer-implemented process for determining potential cancer therapeutic targets by joint modeling of real-world patient survival events in accordance with one or more embodiments of the disclosed subject matter.

FIG. 10 provides a high-level flow diagram of another example computer-implemented process 1000 for determining potential cancer therapeutic targets by joint modeling of real-world patient survival events in accordance with one or more embodiments of the disclosed subject matter. Repetitive description of like elements employed in respective embodiments is omitted for sake of brevity.

At 1002, a device operatively coupled to a processor (e.g., computing device 102), can employ a multi-task learning model (e.g., multi-task survival analysis framework 800) to determine active genetic factors respectively associated with different types of cancer based on cancer survival data and patient genomic data for groups of patients that respectively survived the different types of cancer (e.g., via the active factor identification component 108). At 1004, the device can further determine common active genetic factors of the active genetic factors that are shared between two or more types of cancer of the different types of cancer (e.g., using the disease association component 112).

Figure 11:
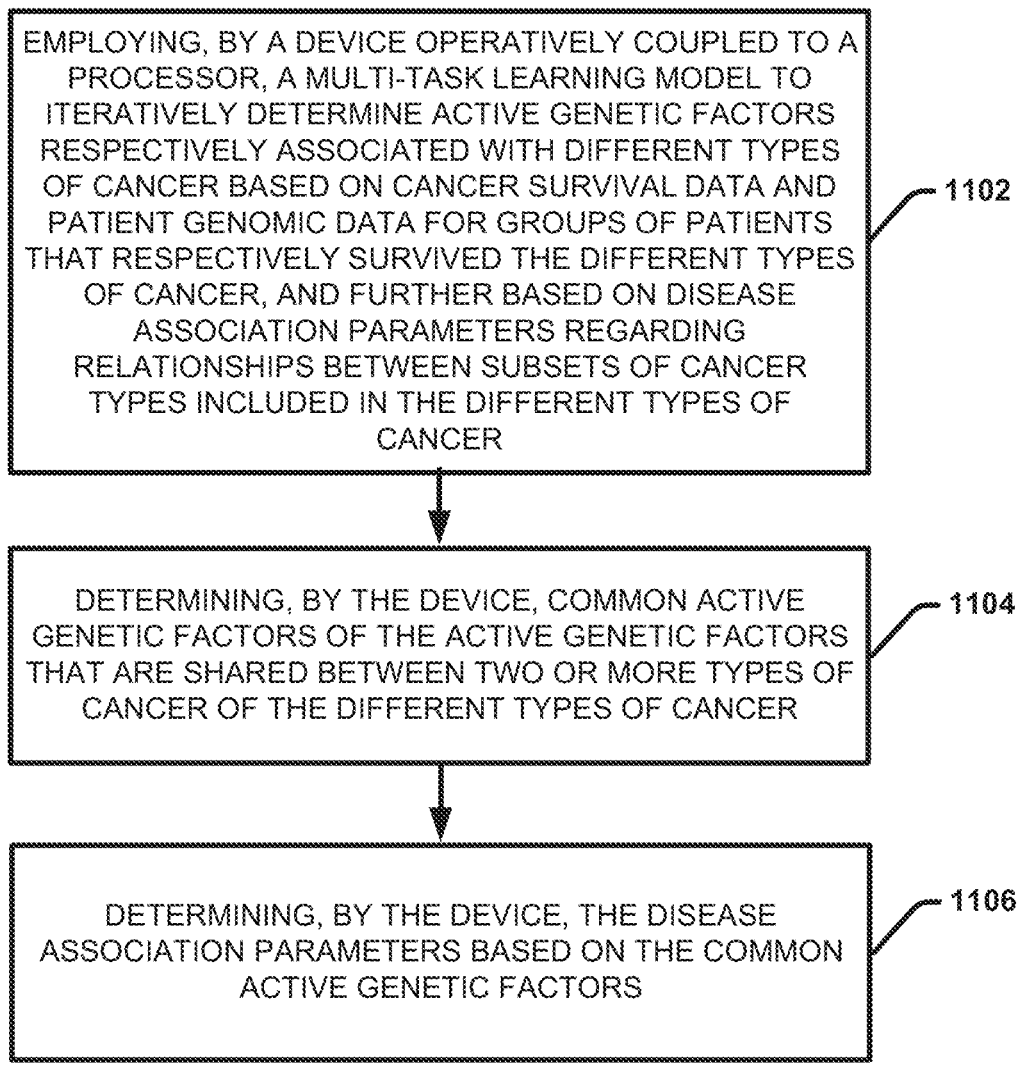
FIG. 11 provides a high-level flow diagram of another example computer-implemented process for determining potential cancer therapeutic targets by joint modeling of real-world patient survival events in accordance with one or more embodiments of the disclosed subject matter.

FIG. 11 provides a high-level flow diagram of another example computer-implemented process 1100 for determining potential cancer therapeutic targets by joint modeling of real-world patient survival events in accordance with one or more embodiments of the disclosed subject matter.

At 1102, a device operatively coupled to a processor (e.g., computing device 102), can employ a multi-task learning model (e.g., multi-task survival analysis framework 800) to iteratively determine active genetic factors respectively associated with different types of cancer based on cancer survival data and patient genomic data for groups of patients that respectively survived the different types of cancer and further based on relationship parameters regarding relationships between subsets of cancer types included in the different types of cancer (e.g., via the active factor identification component 108). At 1104, the device can further determine common active genetic factors of the active genetic factors that are shared between two or more types of cancer of the different types of cancer (e.g., using the disease association component 112). At 1106, the device can determine the disease association parameters based on the common active genetic factors (e.g., using the disease association component 112).

One or more embodiments can be a system, a method, and/or a computer program product at any possible technical detail level of integration. The computer program product can include a computer readable storage medium (or media) having computer readable program instructions thereon for causing a processor to carry out one or more aspects of the present embodiments.

The computer readable storage medium can be a tangible device that can retain and store instructions for use by an instruction execution device. The computer readable storage medium can be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network can comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention can be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions can execute entirely on the entity's computer, partly on the entity's computer, as a stand-alone software package, partly on the entity's computer and partly on a remote computer or entirely on the remote computer or server. In the latter scenario, the remote computer can be connected to the entity's computer through any type of network, including a local area network (LAN) or a wide area network (WAN), or the connection can be made to an external computer (for example, through the Internet using an Internet Service Provider). In some embodiments, electronic circuitry including, for example, programmable logic circuitry, field-programmable gate arrays (FPGA), or programmable logic arrays (PLA) can execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It can be understood that each block of the flowchart illustrations and/or block diagrams, and combinations of blocks in the flowchart illustrations and/or block diagrams, can be implemented by computer readable program instructions.

These computer readable program instructions can be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions can also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions can also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams can represent a module, segment, or portion of instructions, which comprises one or more executable instructions for implementing the specified logical function(s). In some alternative implementations, the functions noted in the blocks can occur out of the order noted in the Figures. For example, two blocks shown in succession may, in fact, be executed substantially concurrently, or the blocks can sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

In connection with FIG. 12, the systems and processes described below can be embodied within hardware, such as a single integrated circuit (IC) chip, multiple ICs, an application specific integrated circuit (ASIC), or the like. Further, the order in which some or all of the process blocks appear in each process should not be deemed limiting. Rather, it should be understood that some of the process blocks can be executed in a variety of orders, not all of which can be explicitly illustrated herein.

Figure 12:
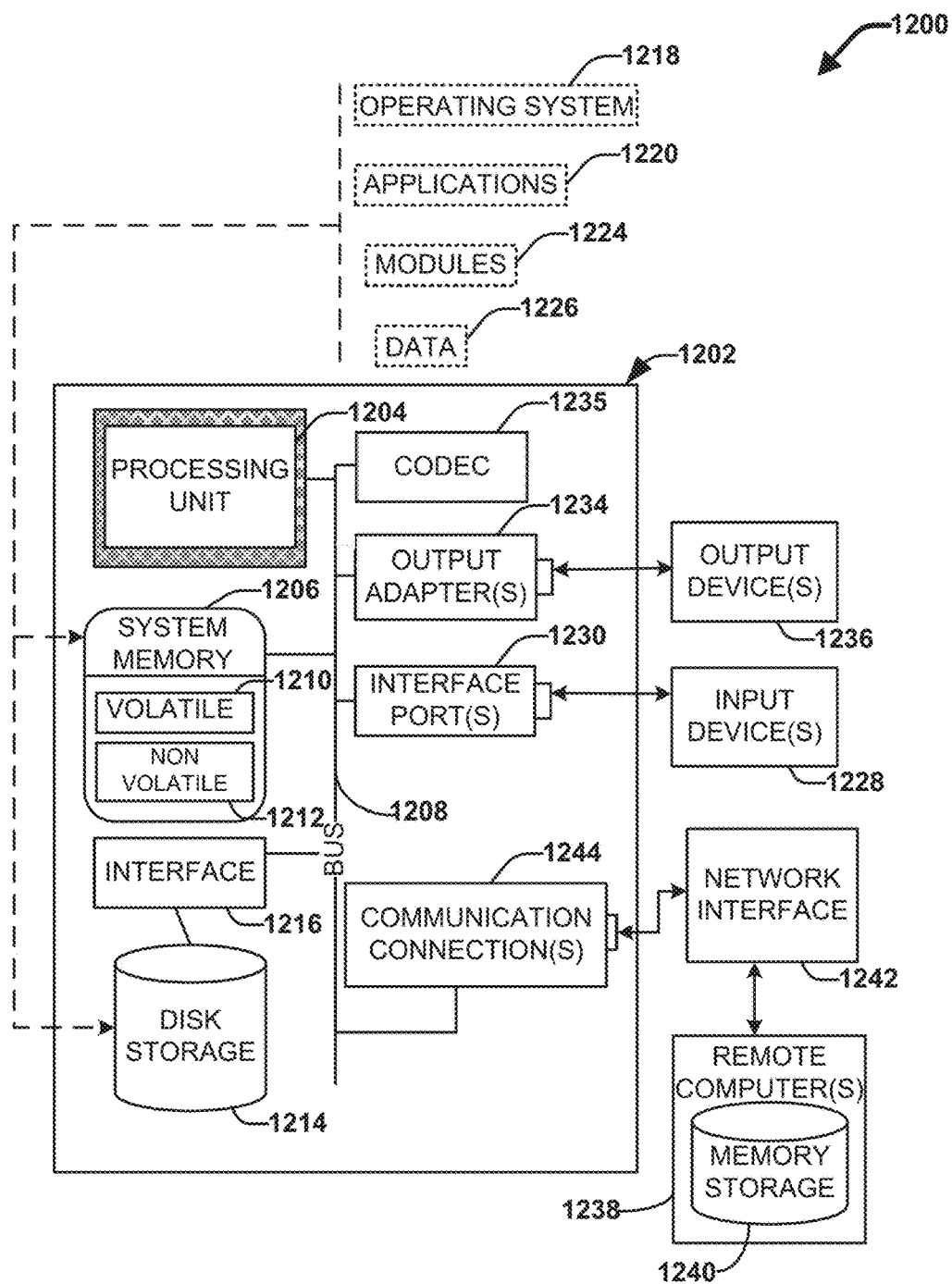
FIG. 12 illustrates a block diagram of an example, non-limiting operating environment in which one or more embodiments described herein can be facilitated.

With reference to FIG. 12, an example environment 1200 for implementing various aspects of the claimed subject matter includes a computer 1202. The computer 1202 includes a processing unit 1204, a system memory 1206, a codec 1235, and a system bus 1208. The system bus 1208 couples system components including, but not limited to, the system memory 1206 to the processing unit 1204. The processing unit 1204 can be any of various available processors. Dual microprocessors and other multiprocessor architectures also can be employed as the processing unit 1204.

The system bus 1208 can be any of several types of bus structure(s) including the memory bus or memory controller, a peripheral bus or external bus, or a local bus using any variety of available bus architectures including, but not limited to, Industrial Standard Architecture (ISA), Micro-Channel Architecture (MSA), Extended ISA (EISA), Intelligent Drive Electronics (IDE), VESA Local Bus (VLB), Peripheral Component Interconnect (PCI), Card Bus, Universal Serial Bus (USB), Advanced Graphics Port (AGP), Personal Computer Memory Card International Association bus (PCMCIA), Firewire (IEEE 13124), and Small Computer Systems Interface (SCSI).

The system memory 1206 includes volatile memory 1210 and non-volatile memory 1212, which can employ one or more of the disclosed memory architectures, in various embodiments. The basic input/output system (BIOS), containing the basic routines to transfer information between elements within the computer 1202, such as during start-up, is stored in non-volatile memory 1212. In addition, according to present innovations, codec 1235 can include at least one of an encoder or decoder, wherein the at least one of an encoder or decoder can consist of hardware, software, or a combination of hardware and software. Although, codec 1235 is depicted as a separate component, codec 1235 can be contained within non-volatile memory 1212. By way of illustration, and not limitation, non-volatile memory 1212 can include read only memory (ROM), programmable ROM (PROM), electrically programmable ROM (EPROM), electrically erasable programmable ROM (EEPROM), Flash memory, 3D Flash memory, or resistive memory such as resistive random access memory (RRAM). Non-volatile memory 1212 can employ one or more of the disclosed memory devices, in at least some embodiments. Moreover, non-volatile memory 1212 can be computer memory (e.g., physically integrated with computer 1202 or a mainboard thereof), or removable memory. Examples of suitable removable memory with which disclosed embodiments can be implemented can include a secure digital (SD) card, a compact Flash (CF) card, a universal serial bus (USB) memory stick, or the like. Volatile memory 1210 includes random access memory (RAM), which acts as external cache memory, and can also employ one or more disclosed memory devices in various embodiments. By way of illustration and not limitation, RAM is available in many forms such as static RAM (SRAM), dynamic RAM (DRAM), synchronous DRAM (SDRAM), double data rate SDRAM (DDR SDRAM), and enhanced SDRAM (ESDRAM) and so forth.

Computer 1202 can also include removable/non-removable, volatile/non-volatile computer storage medium. FIG. 12 illustrates, for example, disk storage 1214. Disk storage 1214 includes, but is not limited to, devices like a magnetic disk drive, solid state disk (SSD), flash memory card, or memory stick. In addition, disk storage 1214 can include storage medium separately or in combination with other storage medium including, but not limited to, an optical disk drive such as a compact disk ROM device (CD-ROM), CD recordable drive (CD-R Drive), CD rewritable drive (CD-RW Drive) or a digital versatile disk ROM drive (DVD-ROM). To facilitate connection of the disk storage 1214 to the system bus 1208, a removable or non-removable interface is typically used, such as interface 1216. It is appreciated that disk storage 1214 can store information related to an entity. Such information might be stored at or provided to a server or to an application running on an entity device. In one embodiment, the entity can be notified (e.g., by way of output device(s) 1236) of the types of information that are stored to disk storage 1214 or transmitted to the server or application. The entity can be provided the opportunity to opt-in or opt-out of having such information collected or shared with the server or application (e.g., by way of input from input device(s) 1228).

It is to be appreciated that FIG. 12 describes software that acts as an intermediary between entities and the basic computer resources described in the suitable operating environment 1200. Such software includes an operating system 1218. Operating system 1218, which can be stored on disk storage 1214, acts to control and allocate resources of the computer 1202. Applications 1220 take advantage of the management of resources by operating system 1218 through program modules 1224, and program data 1226, such as the boot/shutdown transaction table and the like, stored either in system memory 1206 or on disk storage 1214. It is to be appreciated that the claimed subject matter can be implemented with various operating systems or combinations of operating systems.

An entity enters commands or information into the computer 1202 through input device(s) 1228. Input devices 1228 include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices connect to the processing unit 1204 through the system bus 1208 via interface port(s) 1230. Interface port(s) 1230 include, for example, a serial port, a parallel port, a game port, and a universal serial bus (USB). Output device(s) 1236 use some of the same type of ports as input device(s) 1228. Thus, for example, a USB port can be used to provide input to computer 1202 and to output information from computer 1202 to an output device 1236. Output adapter 1234 is provided to illustrate that there are some output devices 1236 like monitors, speakers, and printers, among other output devices 1236, which require special adapters. The output adapters 1234 include, by way of illustration and not limitation, video and sound cards that provide a means of connection between the output device 1236 and the system bus 1208. It should be noted that other devices or systems of devices provide both input and output capabilities such as remote computer(s) 1238.

Computer 1202 can operate in a networked environment using logical connections to one or more remote computers, such as remote computer(s) 1238. The remote computer(s) 1238 can be a personal computer, a server, a router, a network PC, a workstation, a microprocessor based appliance, a peer device, a smart phone, a tablet, or other network node, and typically includes many of the elements described relative to computer 1202. For purposes of brevity, only a memory storage device 1240 is illustrated with remote computer(s) 1238. Remote computer(s) 1238 is logically connected to computer 1202 through a network interface 1242 and then connected via communication connection(s) 1244. Network interface 1242 encompasses wire or wireless communication networks such as local-area networks (LAN) and wide-area networks (WAN) and cellular networks. LAN technologies include Fiber Distributed Data Interface (FDDI), Copper Distributed Data Interface (CDDI), Ethernet, Token Ring and the like. WAN technologies include, but are not limited to, point-to-point links, circuit switching networks like Integrated Services Digital Networks (ISDN) and variations thereon, packet switching networks, and Digital Subscriber Lines (DSL).

Communication connection(s) 1244 refers to the hardware/software employed to connect the network interface 1242 to the bus 1208. While communication connection 1244 is shown for illustrative clarity inside computer 1202, it can also be external to computer 1202. The hardware/software necessary for connection to the network interface 1242 includes, for exemplary purposes only, internal and external technologies such as, modems including regular telephone grade modems, cable modems and DSL modems, ISDN adapters, and wired and wireless Ethernet cards, hubs, and routers.

While the subject matter has been described above in the general context of computer-executable instructions of a computer program product that runs on a computer and/or computers, those skilled in the art will recognize that this disclosure also can or can be implemented in combination with other program modules. Generally, program modules include routines, programs, components, data structures, etc. that perform particular tasks and/or implement particular abstract data types. Moreover, those skilled in the art will appreciate that the inventive computer-implemented methods can be practiced with other computer system configurations, including single-processor or multiprocessor computer systems, mini-computing devices, mainframe computers, as well as computers, hand-held computing devices (e.g., PDA, phone), microprocessor-based or programmable consumer or industrial electronics, and the like. The illustrated aspects can also be practiced in distributed computing environments where tasks are performed by remote processing devices that are linked through a communications network. However, some, if not all aspects of this disclosure can be practiced on stand-alone computers. In a distributed computing environment, program modules can be located in both local and remote memory storage devices.

As used in this application, the terms "component," "system," "platform," "interface," and the like, can refer to and/or can include a computer-related entity or an entity related to an operational machine with one or more specific functionalities. The entities disclosed herein can be either hardware, a combination of hardware and software, software, or software in execution. For example, a component can be, but is not limited to being, a process running on a processor, a processor, an object, an executable, a thread of execution, a program, and/or a computer. By way of illustration, both an application running on a server and the server can be a component. One or more components can reside within a process and/or thread of execution and a component can be localized on one computer and/or distributed between two or more computers. In another example, respective components can execute from various computer readable media having various data structures stored thereon. The components can communicate via local and/or remote processes such as in accordance with a signal having one or more data packets (e.g., data from one component interacting with another component in a local system, distributed system, and/or across a network such as the Internet with other systems via the signal). As another example, a component can be an apparatus with specific functionality provided by mechanical parts operated by electric or electronic circuitry, which is operated by a software or firmware application executed by a processor. In such a case, the processor can be internal or external to the apparatus and can execute at least a part of the software or firmware application. As yet another example, a component can be an apparatus that provides specific functionality through electronic components without mechanical parts, wherein the electronic components can include a processor or other means to execute software or firmware that confers at least in part the functionality of the electronic components. In an aspect, a component can emulate an electronic component via a virtual machine, e.g., within a cloud computing system.

In addition, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Moreover, articles "a" and "an" as used in the subject specification and annexed drawings should generally be construed to mean "one or more" unless specified otherwise or clear from context to be directed to a singular form. As used herein, the terms "example" and/or "exemplary" are utilized to mean serving as an example, instance, or illustration and are intended to be non-limiting. For the avoidance of doubt, the subject matter disclosed herein is not limited by such examples. In addition, any aspect or design described herein as an "example" and/or "exemplary" is not necessarily to be construed as preferred or advantageous over other aspects or designs, nor is it meant to preclude equivalent exemplary structures and techniques known to those of ordinary skill in the art.

As it is employed in the subject specification, the term "processor" can refer to substantially any computing processing unit or device comprising, but not limited to, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components, or any combination thereof designed to perform the functions described herein. Further, processors can exploit nano-scale architectures such as, but not limited to, molecular and quantum-dot based transistors, switches and gates, in order to optimize space usage or enhance performance of entity equipment. A processor can also be implemented as a combination of computing processing units. In this disclosure, terms such as "store," "storage," "data store," "data storage," "database," and substantially any other information storage component relevant to operation and functionality of a component are utilized to refer to "memory components," entities embodied in a "memory," or components comprising a memory. It is to be appreciated that memory and/or memory components described herein can be either volatile memory or nonvolatile memory, or can include both volatile and nonvolatile memory. By way of illustration, and not limitation, nonvolatile memory can include read only memory (ROM), programmable ROM (PROM), electrically programmable ROM (EPROM), electrically erasable ROM (EEPROM), flash memory, or non-volatile random access memory (RAM) (e.g., ferroelectric RAM (FeRAM). Volatile memory can include RAM, which can act as external cache memory, for example. By way of illustration and not limitation, RAM is available in many forms such as synchronous RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), direct Rambus RAM (DRRAM), direct Rambus dynamic RAM (DRDRAM), and Rambus dynamic RAM (RDRAM). Additionally, the disclosed memory components of systems or computer-implemented methods herein are intended to include, without being limited to including, these and any other suitable types of memory.

What has been described above include mere examples of systems and computer-implemented methods. It is, of course, not possible to describe every conceivable combination of components or computer-implemented methods for purposes of describing this disclosure, but one of ordinary skill in the art can recognize that many further combinations and permutations of this disclosure are possible. Furthermore, to the extent that the terms "includes," "has," "possesses," and the like are used in the detailed description, claims, appendices and drawings such terms are intended to be inclusive in a manner similar to the term "comprising" as "comprising" is interpreted when employed as a transitional word in a claim. The descriptions of the various embodiments have been presented for purposes of illustration, but are not intended to be exhaustive or limited to the embodiments disclosed. Many modifications and variations can be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A system, comprising:
a memory that stores computer executable components;
a processor that executes the computer executable components stored in the memory, wherein the computer executable components comprise:
multi-task survival analysis component that trains a multi-task machine learning model to identify active genetic factors respectively associated with the different types of cancer using cancer survival data and patient genomic data for groups of patients, wherein the multi-task machine learning model comprises respective individual survival models for the different types of cancer, and the training the multi-task machine learning model comprises:
iteratively perform until convergence of output data of the multi-task machine learning model satisfies a criterion:
jointly solve the respective individual survival models of the multi-task machine learning model, using input data comprising the cancer survival data and the patient genomic data for the groups of patients that respectively survived the different types of cancer to generate the output data that identifies the active genetic factors respectively associated with the different types of cancer, and common active genetic factors of the active genetic factors that are shared between two or more types of cancer of the different types of cancer, and
update the input data with the active genetic factors and the common active genetic factors.

2. The system of claim 1, wherein the multi-task survival analysis component further comprises:
a scoring component that determines, using the multi-task machine learning model, scores for the active genetic factors that respectively represent degrees of association between the active genetic factors and the different types of cancer with which the active genetic factors are respectively associated.

3. The system of claim 2, wherein the multi-task survival analysis component further comprises:
a selection component that selects, using the multi-task machine learning model, one or more active genetic factors of the active genetic factors as gene therapy targets based on the scores respectively associated with the one or more active genetic factors.

4. The system of claim 1, wherein the the output data further comprises relationship parameters representative of relationships between subsets of the different types of cancer based on a number of the common active genetic factors shared between respective types of cancer included in the subsets.

5. The system of claim 1, wherein the jointly solving the respective individual survival models of the multi-task machine learning model further determines association scores for the subsets based on the number of the common active genetic factors shared between the respective types of cancer included in the subsets, wherein the association scores reflect degrees to which the respective types of cancer are related.

6. The system of claim 4, wherein the update of the input data comprises update the input data with the relationship parameters.

7. The system of claim 1, wherein the multi-task survival analysis component further comprises:
an indexing component that generates, using the multi-task machine learning model, based on the common active genetic factors, an indexed data structure that identifies, for respective common active genetic factors of the common active genetic factors, each of the different types of cancer associated with the respective common active genetic factors.

8. The system of claim 1, wherein the input data further comprises historical disease association information for the different types of cancer comprising historical relationship parameters representative of historical relationships between subsets of the different types of cancer.

9. The system of claim 8, wherein the criterion comprises a difference between the output data from an iteration using the multi-task machine learning model and a previous output data from a previous iteration using the multi-task machine learning model being less than a defined degree of deviation.

10. A computer implemented method, comprising:
training, by a device operatively coupled to a processor, a multi-task machine learning model to determine active genetic factors respectively associated with different types of cancer based on cancer survival data and patient genomic data for groups of patients that respectively survived the different types of cancer, wherein the multi-task machine learning model comprises respective individual survival models for the different types of cancer, and the training comprises:
  iteratively performing until convergence of output data of the multi-task machine learning model satisfies a criterion:
    jointly training the respective individual survival models of the multi-task machine learning model, using the input data comprising the cancer survival data and the patient genomic data for the groups of patients that respectively survived the different types of cancer to generate the output data that identifies the active genetic factors respectively associated with the different types of cancer, and common active genetic factors of the active genetic factors that are shared between two or more types of cancer of the different types of cancer, and
    updating the input data with the active genetic factors and the common active genetic factors.

11. The computer implemented method of claim 10, wherein the training further comprises:
  determining, using the multi-task machine learning model, scores for the active genetic factors that respectively represent degrees of association between the active genetic factors and the different types of cancer with which the active genetic factors are respectively associated; and
  selecting, using the multi-task machine learning model, one or more active genetic factors of the active genetic factors as gene therapy targets based on the scores respectively associated with the one or more active genetic factors.

12. The computer implemented method of claim 10, wherein the output data further comprises relationship parameters representative of relationships between subsets of the different types of cancer based on a number of the common active genetic factors shared between respective types of cancer included in the subsets.

13. The computer implemented method of claim 10, wherein the jointly solving the respective individual survival models of using the multi-task machine learning model, further determines association scores for the subsets based on the number of the common active genetic factors shared between the respective types of cancer included in the subsets, wherein the association scores reflect degrees to which the respective types of cancer are related.

14. The computer implemented method of claim 12, wherein the updating the input data comprises updating the input data with the relationship parameters.

15. The computer implemented method of claim 10, wherein the criterion comprises a difference between the output data from an iteration using the multi-task machine learning model and a previous output data from a previous iteration using the multi-task machine learning model being less than a defined degree of deviation.

16. A computer program product for determining potential cancer gene therapy targets, the computer program product comprising a computer readable storage medium having program instructions embodied therewith, the program instructions executable by a processing component to cause the processing component to:
  train a multi-task machine learning model to determine active genetic factors respectively associated with different types of cancer based on cancer survival data and patient genomic data for groups of patients that respectively survived the different types of cancer, wherein the multi-task machine learning model comprises respective individual survival models for the different types of cancer, and the training comprises:
    iteratively performing until convergence of output data of the multi-task machine learning model satisfies a criterion:
      jointly training the respective individual survival models of the multi-task machine learning model, using the input data comprising the cancer survival data and the patient genomic data for the groups of patients that respectively survived the different types of cancer to generate the output data that identifies the active genetic factors respectively associated with the different types of cancer, and common active genetic factors of the active genetic factors that are shared between two or more types of cancer of the different types of cancer, and
      updating the input data with the active genetic factors and the common active genetic factors.

17. The computer program product of claim 16, wherein the training further comprises:
  determine, using the multi-task machine learning model, scores for the active genetic factors that respectively represent degrees of association between the active genetic factors and the different types of cancer with which the active genetic factors are respectively associated; and
  select, using the multi-task machine learning model, one or more active genetic factors of the active genetic factors as the potential cancer gene therapy targets based on the scores respectively associated with the one or more active genetic factors.

18. The computer program product of claim 16, wherein the output data further comprises relationship parameters representative of relationships between subsets of the different types of cancer based on a number of the common active genetic factors shared between respective types of cancer included in the subsets.

19. The computer program product of claim 16, wherein the updating the input data comprises updating the input data with the relationship parameters.

20. The computer program product of claim 16, wherein the criterion comprises a difference between the output data from an iteration using the multi-task machine learning model and a previous output data from a previous iteration using the multi-task machine learning model being less than a defined degree of deviation.

* * * * *